United States Patent [19]
Yasuda et al.

[11] Patent Number: 6,133,431
[45] Date of Patent: Oct. 17, 2000

[54] ADSORBENT FOR IMMUNOGLOBULINS AND COMPLEXES THEREOF, ADSORPTION METHOD, AND ADSORPTION DEVICE

[75] Inventors: Takamune Yasuda, Kobe; Osamu Odawara, Takasago; Eiji Ogino, Kobe; Michio Nomura, Kakogawa; Takahisa Nakai; Takashi Asahi, both of Kobe; Nobutaka Tani, Osaka, all of Japan

[73] Assignee: Kaneka Corporation, Osaka, Japan

[21] Appl. No.: 09/117,233

[22] PCT Filed: Jan. 24, 1997

[86] PCT No.: PCT/JP97/00161

§ 371 Date: Oct. 20, 1998

§ 102(e) Date: Oct. 20, 1998

[87] PCT Pub. No.: WO97/26930

PCT Pub. Date: Jul. 31, 1997

[30] Foreign Application Priority Data

Jan. 25, 1996 [JP] Japan .................................. 8-011281

[51] Int. Cl.[7] ............................. A61K 39/00; C07K 17/00
[52] U.S. Cl. ..................... 530/413; 210/660; 210/674; 424/140.1; 604/5.01; 604/5.02
[58] Field of Search ..................... 424/140.1; 436/507, 436/824; 530/413; 210/660, 674; 604/5, 6, 5.01, 5.02

[56] References Cited

U.S. PATENT DOCUMENTS

| | | | |
|---|---|---|---|
| 4,614,513 | 9/1986 | Bensinger | 604/6 |
| 5,108,894 | 4/1992 | Bjorck et al. | 435/6 |
| 5,306,812 | 4/1994 | Zanetti et al. | 530/413 |
| 5,312,901 | 5/1994 | Fahnestock | 530/350 |

FOREIGN PATENT DOCUMENTS

| | | |
|---|---|---|
| 1-104273 | 4/1989 | Japan . |
| 1-158970 | 6/1989 | Japan . |
| 6-263795 | 9/1994 | Japan . |
| 7-0p92167 | 4/1995 | Japan . |
| WO 87/05025 A1 | 8/1987 | WIPO . |
| WO 89/04675 A1 | 6/1989 | WIPO . |

OTHER PUBLICATIONS

*Affinity Chromatography Principles and Methods*, Pharmacia Fine Chemicals, 1974, p. 6.
Akesson, P. et al., *Mol. Immunol.*, vol. 27, pp. 523–531 (1990).
Björck, L., *J. Immunol.*, vol. 140, pp. 1194–1197 (1988).
Fahnestock, S.R. et al., *J. Bacteriol.*, vol. 167, pp. 870–880 (1986).
Guss, B. et al., *Embo J.*, vol. 5, pp. 1567–1575 (1986).
Sjöbring, U. et al., *J. Biol. Chem.*, vol. 266, pp. 399–405 (1991).

*Primary Examiner*—David Saunders
*Attorney, Agent, or Firm*—Fish & Neave; James F. Haley, Jr.; Stanley D. Liang

[57] ABSTRACT

An adsorbent that exhibits a high specificity in adsorbing immunoglobulins and/or complexes thereof, is extremely reduced in the lowering of the adsorption characteristic during sterilization or storage, is highly stable and safe, and is prepared by immobilizing on a water-insoluble support either a peptide derivative which has undergone at least one of the deletion, substitution, insertion, or addition of amino acids in a peptide having a specified amino acid sequence or an amino acid sequence, or the above peptide derivative which has undergone the addition of Lyn or Cys at the amino and/or carboxyl terminal thereof; a device for adsorption and removal made by packing the adsorbent in a vessel equipped with effluent preventing means; and a method of adsorbing and removing immunoglobulins and/or complexes thereof contained in the blood, plasma or other body fluids with the adsorbent.

20 Claims, 7 Drawing Sheets

ADSORBENT FOR IMMUNOGLOBULINS AND COMPLEXES THEREOF, ADSORPTION METHOD, AND ADSORPTION DEVICE

TECHNICAL FIELD

The present invention relates to an adsorbent and an adsorption device for adsorbing immunoglobulins and/or immunoglobulin complexes, and a method for adsorbing and removing immunoglobulins and/or immunoglobulin complexes.

BACKGROUND ART

In recent years, it has become clear that, in autoimmune diseases such as rheumatoid arthritis, systemic lupus erythematoses, Guillain-Barre syndrome, and idiopathic thrombocytopenic purpura, or in diseases such as glomerular nephritis, rejection of transplanted organs, tumor, and infectious disease, immunoglobulins and/or immunoglobulin complexes present in the blood have a close relationship with the cause or progress of diseases and/or phenomena.

Under the above-mentioned circumstance, several adsorbing and removing materials have been utilized in the hope of preventing the progress of the above-mentioned diseases, relieving the conditions, and furthermore promoting healing by specifically adsorbing and removing immunoglobulins and/or immunoglobulin complexes from the body fluid such as the blood and the plasma. For example, an immune adsorbent (Japanese Laid-open Publication No. 62-242628) in which protein A capable of binding to immunoglobulins is immobilized onto a silica matrix is known as an adsorbent which is highly specific to immunoglobulin G and immunoglobulin complexes thereof. Furthermore, an adsorbent (Japanese Laid-open Publication No. 57-122875) for immunoglobulins and/or immunoglobulin complexes in which a hydrophobic compound is immobilized onto an insoluble carrier has already been clinically applied in Japan.

However, the adsorbent which has been used (e.g., the above-mentioned adsorbent for protein A) has disadvantages. Specifically, protein A, which is a functional group, is a heterogenous protein having a molecular weight of about 42,000 daltons derived from *Staphylococcus aureus,* so that when the adsorbent is used in contact with the body fluid, protein A is eluted and its antigenicity may cause side effects. Also there is a problem of stability during sterilization of the adsorbent, therefore sterilization method is limited. Additionally, storage stability is not sufficient after protein A is immobilized onto a silica matrix; and the like. Furthermore, the adsorbent for immunoglobulins and/or immune complexes thereof described in Japanese Laid-open Publication No. 57-122875 has the disadvantages of poor adsorbing characteristics such as adsorption specificity to a substance of interest and adsorbing capacity (I. Amano et al., "Blood purification therapy, 1st part", Japanese Journal of Clinical Medicine, Vol. 49, pp. 649–654 (1991 sup.). Accordingly, in terms of the safety, stability, adsorbing specificity, adsorbing capacity, and the like, the conventionally known adsorbent for adsorbing immunoglobulins and/or immunoglobulin complexes is not necessarily suitable for use in treating diseases caused by the presence of the above-mentioned pathogenic immunoglobulins and/or immunoglobulin complexes in the body fluid.

DISCLOSURE OF THE INVENTION

The objective of the present invention is to provide an adsorbent with high stability and safety which has high adsorbing specificity to immunoglobulins and/or immunoglobulin complexes and whose adsorbing characteristics decrease less during sterilization or storage, an adsorption device using the adsorbent, and a method for adsorbing and removing immunoglobulins and/or immunoglobulin complexes.

The inventors of the present invention considered the factors that (1) various proteins are known to be immunoglobulin binding proteins, such as protein A, protein G, protein H, protein L, and a rheumatoid factor (N. Tsuchiya, Clinical Immunology, Vol. 23, pp. 896–903 (1991); P. Akesson et al., *Mol. Immunol.,* Vol. 27, pp. 523–531 (1990); and L. Bjorck, *J. Immunol.,* pp. 1194–1197 (1988)) have substantially high adsorbing specificity to immunoglobulins and/or immunoglobulin complexes, (2) a peptide having tens of amino acid residues or about ten or less amino acid residues has antigenicity to a living organism which is much smaller than that of a heterogenous naturally-occurring macromolecule protein, and (3) such a short peptide has high stability which is represented by thermal stability, particularly high stability to sterilization and storage stability. We generated various peptides from immunoglobulin binding proteins and studied them. As a result, we succeeded in obtaining a peptide which has high thermal stability, drug stability, and/or sterilization stability, when determined based on high adsorbing specificity and adsorbing capacity with respect to immunoglobulins and/or immunoglobulin complexes as indexes, and which is unlikely to have side effects caused by antigenicity, by using a partial peptide of protein G.

Protein G is one of the immunoglobulin binding proteins, which has a molecular weight of about 50,000 daltons and is present on a bacteria cell wall of Streptococcus. The cDNA of protein G has already been cloned. Based on an amino acid sequence predicted from the cDNA, protein G is assumed to consist of 448 amino acid residues. Furthermore, it has been assumed that several similar repeated amino acid sequences are present in the predicted amino acid sequence, and that the repeated amino acid sequences are binding domains to albumin and immunoglobulins. See, for example, S. R. Fabhestock et al., *J. Bacteriol.,* Vol. 167, pp. 870–880 (1986); U. Sjobring et al., *J. Biol. Chem.,* Vol. 266, pp. 399–405 (1991). In B. Guss et al., *EMBO J.,* Vol. 5, pp. 1567–1575 (1986), a repeated amino acid sequence region represented by C1, C2, or C3 suggesting an immunoglobulin (IgG) binding domain in the sequence of protein G is described. When common amino acids and amino acids which are not common in each amino acid sequence of C1, C2, and C3 are summarized, the amino acid sequence of the IgG binding domain is as represented by SEQ ID NO: 1 of Sequence Listing.

Furthermore, the inventors also studied sterilization stability of C3 peptides to γ-ray sterilization by binding a C3 peptide, which is one of the above-mentioned peptides, to a carrier, and found sterilization stability of C3 peptides was not necessarily sufficient. Then, we generated various peptides and studied them for sterilization stability by successively modifying any amino acid of a C3 peptide into another amino acid by using a genetic engineering technique. As a result, we obtained a peptide which has high affinity for immunoglobulins and/or immunoglobulin complexes, in which the adsorbing capacity of a peptide ligand is hardly damaged by γ-ray sterilization, and which has excellent thermal stability and drug stability, thereby achieving the present invention.

In an adsorbent for adsorbing immunoglobulins and/or immunoglobulin complexes of the present invention, a peptide capable of adsorbing immunoglobulins and/or immunoglobulin complexes is immobilized onto a water-insoluble carrier, and the peptide has one or two kinds of amino acid sequences selected from the amino acid sequences represented by SEQ ID NO:1 of Sequence Listing.

In an adsorbent for adsorbing immunoglobulins and/or immunoglobulin complexes of the present invention, a peptide derivative is immobilized onto a water-insoluble carrier, and the peptide derivative includes at least one of deletion, substitution, insertion, and addition of an amino acid with respect to the amino acid sequences represented by SEQ ID NO: 1 of Sequence Listing, and is capable of adsorbing immunoglobulins and/or immunoglobulin complexes.

In a preferred embodiment, at least one of the properties of thermal stability, drug stability, γ-ray sterilization stability, and high-pressure vapor sterilization stability of the above-mentioned peptide derivative is improved over that of a peptide having the amino acid sequence represented by SEQ ID NO: 1.

In a preferred embodiment, the above-mentioned peptide derivative includes the amino acid sequence represented by SEQ ID NO: 3.

In a preferred embodiment, (Lys)n or (Cys)m is added to an amino terminus and/or a carboxyl terminus of the above-mentioned peptide or peptide derivative, wherein n and m are integers of 0 to 9.

In a preferred embodiment, the above-mentioned peptide br peptide derivative consists of an amino acid sequence of 70 amino acids or less.

In a preferred embodiment, the adsorbent is subjected to high-pressure vapor sterilization.

In a preferred embodiment, the adsorbent is subjected to γ-ray sterilization.

In a preferred embodiment, the above-mentioned water-insoluble carrier is porous.

In a preferred embodiment, the above-mentioned water-insoluble carrier is hydrophilic.

In a preferred embodiment, a molecular weight of the exclusion limit of the above-mentioned water-insoluble carrier is in the range of about 150,000 to about 5,000,000.

In a preferred embodiment, the adsorbent of the present invention is used for adsorbing and removing immunoglobulins and/or immunoglobulin complexes present in the blood, plasma, or other body fluids obtained from a living organism.

A method for adsorbing and removing immunoglobulins and/or immunoglobulin complexes of the present invention includes the step of bringing any of the above-mentioned adsorbent into contact with a solution containing immunoglobulins and/or immunoglob complexes.

In a device for adsorbing and removing immunoglobulins and/or immunoglobulin complexes of the present invention, any of the above-mentioned adsorbents is accommodated in a vessel having an inlet and an outlet for a solution, and the device comprises effluent preventing means for preventing the adsorbent from flowing out of the vessel.

In a preferred embodiment, the above-mentioned solution containing immunoglobulins and/or immunoglobulin complexes is the blood, plasma, or other body fluids obtained from a living organism.

BEST MODE FOR CARRYING OUT THE INVENTION

I. Definition

Figure 1:
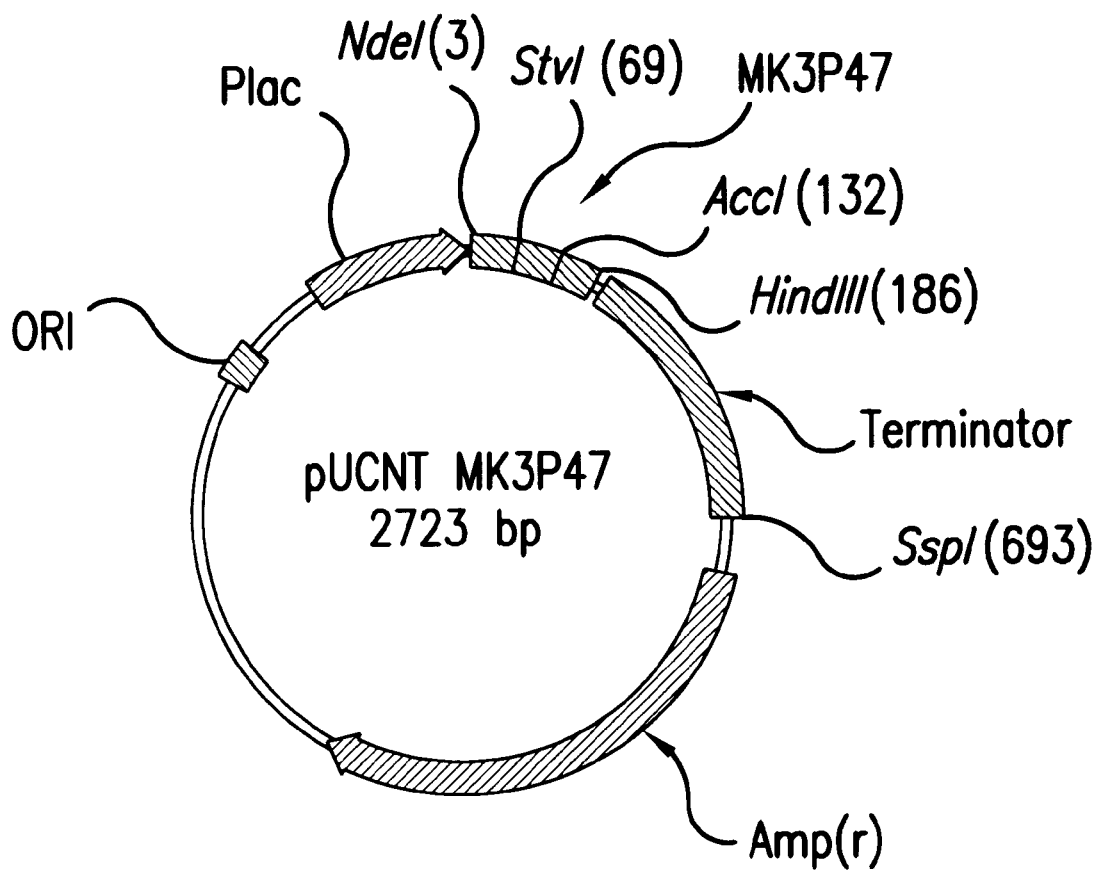
FIG. 1 is a schematic diagram of plasmid pUCNTMK3P47 for expressing MK3P47 peptide. In a vector for expressing other peptides described in the examples, DNA encoding MK3P47 peptide inserted between NdeI-HindIII of pUCNTMK3P47 is replaced by DNA encoding other peptides described in each example.

In the present specification, various kinds of amino acid residues are abbreviated as follows: Ala; L-alanine residue, Asp; L-aspartic acid residue, Asn; L-asparagine residue, Cys; L-cysteine residue, Gln; L-glutamine residue, Glu; L-glutamic acid residue, Gly; L-glycine residue, Ile; L-isoleucine residue, Leu; L-leucine residue, Lys; L-lysine residue, Phe; L-phenylalanine residue, Thr; L-threonine residue, Trp; L-tryptophan residue, Tyr; L-tyrosine residue, and Val; L-valine residue. Furthermore, in the present specification, an amino acid sequence of a peptide is described in such a general manner that the amino terminus of the peptide (hereinafter, referred to as the "N-terminus") is positioned on the left side, and the carboxyl terminus of the peptide (hereinafter, referred to as the "C-terminus") is positioned on the right side.

In the present specification, a peptide derivative refers to a peptide containing at least one of deletion, substitution, insertion, or addition of an amino acid in the amino acid sequences represented by SEQ ID NO: 1 of Sequence Listing.

In the present specification, thermal stability refers to the level of a thermal denaturation temperature of a peptide derivative. The term "having excellent thermal stability" refers to that a thermal denaturation temperature of a peptide derivative is higher than that of a peptide consisting of the amino acids represented by SEQ ID NO: 1. As an example of a method for measuring a thermal denaturation temperature, there is a method for measuring a thermal denaturation temperature in an aqueous solution such as saline by using an adiabatic type differential scanning calorimeter.

In the present specification, drug stability refers to a denaturation ratio of a peptide after drug treatment with respect to the peptide which is not subjected to drug treatment. The term "having excellent drug stability" refers to that a denaturation ratio of a peptide derivative is lower than that of a peptide consisting of the amino acids represented by SEQ ID NO: 1. As an example of a method for determining a denaturation ratio of a peptide, there is a method for comparing the fluorescent intensity of a peptide measured after the treatment in an aqueous solution containing an appropriate concentration of guanidine hydrochloride at 30° C. for 10 minutes with the fluorescent intensity of a peptide before the treatment.

In the present specification, a γ-ray sterilization method refers to a method for killing microorganisms by irradiating them with γ-rays from a radiation source containing radioactive isotopes described in *(i) Radiation Methods: An irradiation method as a "Sterilization method"*, described in Japanese pharmacopoeia. As an example of the γ-ray sterilization method, there is a method for irradiating each adsorbent in an aqueous solution by using a radiation source containing cobalt 60 and the like γ-ray sterilization stability refers to a ratio of the capacity of a peptide derivative subjected to γ-ray sterilization to adsorb immunoglobulins, with respect to the capacity of the peptide not subjected to γ-ray sterilization to adsorb immunoglobulins. The term "having excellent γ-ray sterilization stability" refers to that a remaining ratio of the adsorbing capacity of a peptide derivative is higher than that of a peptide consisting of the amino acids represented by SEQ ID NO: 1.

In the present specification, a high-pressure vapor sterilization method refers to a method for killing microorganisms by heating them in saturated stream at an appropriate temperature under an appropriate pressure described in *(iii) High-pressure Vapor Methods: A heating method as a "Sterilization method"*, described in Japanese pharmacopoeia. As an example of the high-pressure vapor sterilization method, there is a method for subjecting an adsorbent in an aqueous solution to an autoclave treatment at 121° C. for 20 minutes. High-pressure vapor sterilization stability refers to a ratio of the capacity of a peptide derivative before the high-pressure vapor sterilization treatment to adsorb immunoglobulins, with respect to the capacity of the peptide derivative subjected to the treatment to adsorb immunoglobulins. The term "having excellent high-pressure vapor sterilization stability" refers to that a remaining ratio of the adsorbing capacity of a peptide derivative is higher than that of a peptide consisting of the amino acids represented by SEQ ID NO: 1.

II. Preferred Embodiment

Hereinafter, the present invention will be described by way of preferred embodiments. It should be noted that the present invention is not limited by the following description.

As a peptide used for an adsorbent of the present invention, a peptide having the amino acid sequence represented by SEQ ID NO: 3 of Sequence Listing is preferably used. The most important features in this amino acid sequence region are that the C-terminus sequence (amino acid sequence from position 47 to position 56 of the peptide represented by SEQ ID NO: 1) contained in C1, C2, and C3 of protein G is Asp Ala Thr Lys Thr Phe Thr Val Thr Glu, whereas corresponding sequence in the amino acid sequence represented by SEQ ID NO: 3 is Pro Ala Thr Lys Thr Phe Thr Val Thr Glu.

More specifically, at position 47, an amino acid (Asp) is replaced by another amino acid (Pro). It was found that due to this amino acid substitutions, the sterilization stability (in particular, stability with respect to γ-ray sterilization) of the peptide represented by SEQ ID NO: 3 remarkably improves, and the drug stability based on a denaturation concentration by guanidine hydrochloride as an index and the thermal stability based on a thermal denaturation point measured by calorimetry as an index also improves. Furthermore, the pH stability of the peptide represented by SEQ ID NO: 3 was excellent. Recently, it is common to replace an amino acid by a genetic engineering technique, and thus, it is a well-known technique to study the improvement of characteristics of a peptide and a protein by amino acid substitution. However, there have been no examples showing that the sterilization stability of a peptide or a protein remarkably improved by replacing only one amino acid by another. Thus, the above-mentioned fact is a surprising finding.

An adsorbing functional group peptide used for the adsorbent of the present invention has one or two kinds of amino acid sequences selected from the amino acid sequences represented by SEQ ID NO: 1 of Sequence Listing, and may contain the same kind of repeated amino acid sequences or a combination of different amino acid sequences. For example, a peptide selected from the amino acid sequences represented by SEQ ID NO: 1 of Sequence Listing may contain only one kind of peptide selected from the peptides corresponding to C1, C2, and C3 in the amino acid sequence of protein G described in B. Guss et al., EMBO J., Vol. 5, pp. 1567–1575 (1986). Alternatively, the peptide may contain one selected kind of repeated peptides (i.e., a peptide containing at least two C1's, at least two C2's, or at least two C3's), or may contain two selected kinds of amino acid sequences (i.e., a peptide containing C1 and C2, C1 and C3, or C2 and C3). Furthermore, the peptide may contain two selected kinds of amino acid sequences arbitrarily repeated (e.g., a peptide containing two C1's and one C2, two C1's and one C3, one C2 and two C3's, two C1's and two C3's, or the like). The peptide may consist of substantially only the amino acid sequence represented by SEQ ID NO: 1 of Sequence Listing, or may further contain any amino acid residue or amino acid sequence at the N-terminus and/or the C-terminus of the amino acid sequence.

An adsorbing function group peptide derivative used for the adsorbent of the present invention is a peptide having at least one kind of amino acid sequence containing at least one of deletion, substitution, insertion, and/or addition of an amino acid with respect to the amino acid sequences represented by SEQ ID NO: 1 of Sequence Listing, which may consist of only one kind of amino acid sequence or the combination of at least two kinds of amino acid sequences. In the case of addition, any amino acid residue or amino acid sequence may be placed at the N-terminus and/or the C-terminus of the amino acid sequence. A preferred peptide derivative has an amino acid sequence in which (Lys)n or (Cys)m is added to the N-terminus and/or the C-terminus with respect to at least one kind of amino acid sequence selected from the amino acid sequences represented by SEQ ID NO: 3 (herein, n and m are integers of 0 to 9). In particular, a peptide derivative having (Cys)m at the C-terminus of the amino acid sequence is more preferable.

Such a peptide derivative can have the capacity to adsorb immunoglobulins and/or immunoglobulin complexes in the body fluids, and more preferably has the excellent adsorbing capacity after the high-pressure vapor sterilization treatment, heat treatment, drug treatment, or γ-ray sterilization treatment, compared with the peptides represented by SEQ ID NO: 1.

The combination of the above-mentioned peptide and peptide derivative can be used for the adsorbent of the present invention.

The peptide or the peptide derivative used for the adsorbent of the present invention may be produced by a generally used peptide synthesis method, (e.g., a solid phase synthesis method, a liquid phase synthesis method such as a stepwise elongation method, and a fragment condensation method), or by a gene manipulation method including the steps of connecting DNA encoding a peptide or a peptide derivative to a vector and introducing the vector into a host to produce a recombinant peptide or a recombinant peptide derivative.

In chemical synthesis of a peptide or a peptide derivative, it makes manipulation easier to apply a solid phase synthesis method rather than a liquid phase synthesis method. According to the solid phase synthesis method, for example, a peptide or a peptide derivative can be synthesized as follows. (1) An amino acid corresponding to the C-terminus of a peptide to be synthesized is bound to a support insoluble in an organic solvent. (2) Each corresponding amino acid protecting a functional group such as an α-amino group other than an α-carboxy group is bound to the amino acid binding to the substrate successively toward the N-terminus direction by condensation reaction. (3) A protective group of the α-amino group of the bound amino acid is removed. (4) The steps (1) to (3) are alternately repeated. As a result of these steps of manipulation, a peptide chain is elongated to obtain a peptide with a desired length.

After the peptide of interest is obtained, a peptide chain is cleaved from the support, and protective groups are removed. For this purpose, hydrogen fluoride is often used. However, in terms of safety and ease of handling, it is appropriate to use trifluoroacetic acid (hereinafter, referred to as "TFA"). More specifically, the peptide of interest is reacted in 95% TFA containing 1,2-ethanedithiol and anisole (1:3), whereby the peptide is cleaved from the substrate and the protecting groups are removed. Thus, a crude peptide is collected. The crude peptide is precipitated with ethyl ether, whereby a crude purified peptide is obtained.

The crude purified peptide thus obtained can be purified by various methods known to those skilled in the art. For example, the crude purified peptide is subjected to high performance liquid chromatography (hereinafter, referred to as "HPLC") using a reverse phase system column, whereby the peptide can be fractionated, collected, and purified. HPLC conditions should be optimized based on a system used generally for purifying a protein. A fraction corresponding to the peak of chromatography thus obtained, and lyophilized. The resultant purified peptide fraction is subjected to primary sequence analysis by an amino acid sequencer and amino acid composition analysis, whereby a synthesized peptide is confirmed.

In the case where a recombinant peptide or a recombinant peptide derivative is produced by a gene recombination method, based on an amino acid sequence of a peptide of interest, DNA encoding the amino acid sequence is synthesized and introduced into a phage or a plasmid vector. The resultant phage or plasmid vector is integrated into an appropriate microorganism (e.g., *E. coli*) to select and obtain a transformant, and the transformant is cultured by a known method. It is well within the skill of those in the art to purify and isolate a peptide of interest from this culture supernatant or cells. Furthermore, as long as an appropriate vector is selected, yeast, *Bacillus subtilis*, and the like can be easily utilized as a host.

A water-insoluble carrier used as a support of the adsorbent of the present invention is not particularly limited. Examples of the water-insoluble carrier used in the present invention include inorganic carriers such as glass beads and silica gels; organic carriers made of synthetic macromolecules such as cross-linked polyvinyl alcohol, cross-linked polyacrylate, cross-linked polyacrylamide, and cross-linked polystyrene or polysaccharides such as crystalline cellulose, cross-linked cellulose, cross-linked agarose, and cross-linked dextran; and complexes carriers obtained by combining these organic carriers and inorganic carriers, such as a combination of two kinds of organic carriers and a combination of an organic carrier and an inorganic carrier. In the case of using a carrier for hemocatharsis, it is necessary to consider effects of a carrier on a complement system, a clotting system, and the like, when the carrier comes into contact with blood components. Therefore, hydrophilic carriers, which have relatively less possibility of non-specific adsorption and have satisfactory adsorbing selectivity with respect to immunoglobulins and/or immunoglobulin complexes, are preferably used. In the present specification, a hydrophilic carrier refers to a carrier in which, when a compound forming a carrier is formed into a flat plate, a contact angle between the flat plate and the water becomes about 60° or less. Examples of such a carrier include, but are not limited to, carriers formed of polysaccharides such as cellulose, chitosan, Sepharose and dextran, polyvinyl alcohol, a saponified ethylene-vinyl acetate copolymer, polyacrylamide, polyacrylic acid, polymethacrylic acid, poly(methyl methacrylate), polyacrylic acid-grafted polyethylene, polyacrylamide-grafted polyethylene, and glass, or carriers formed of derivatives thereof.

Among the above-mentioned water-insoluble carriers, those having an —OH group have excellent adsorbing capacity and adsorbing selectivity. Above all, a porous cellulose gel has the following excellent points:

(1) The porous cellulose gel is stiff because of relatively high mechanical strength, so that it is unlikely to be damaged or generate fine powders due to stirring. Thus, when the body fluid is passed through a column packed with the gel at a high speed, the gel is unlikely to cause compaction or clogging in the column. Furthermore, the porous structure of the gel is unlikely to change due to high-pressure vapor sterilization, and the like.

(2) Being formed of cellulose, the porous cellulose gel is hydrophilic. Since a number of hydroxyl groups available to binding of a ligand are present on the gel, there is little possibility of non-specific adsorption.

(3) Since the porous cellulose gel keeps its relatively high strength even in the case where a pore area is enlarged, an adsorbing capacity which is comparable to a soft gel is obtained.

(4) The porous cellulose gel has higher safety factor than that of a synthetic macromolecular gel.

Thus, the porous cellulose gel is one of those most suitable for use in the present invention. The carrier used in the present invention is not limited to those described above. The above-mentioned carriers may be used singly, or any two or more kinds thereof may be mixed.

A primary property required of the water-insoluble carrier used in the present invention is that the carrier has a number of pores with an appropriate size, i.e., the carrier is porous. Immunoglobulins and/or immunoglobulin complexes which are to be adsorbed by the adsorbent of the present invention have a molecular weight in a wide range of about 160,000 to about 1,000,000, and thus, they cannot be specified. Therefore, in order for the adsorbent to efficiently adsorb a protein, it is preferable that immunoglobulins and/or immunoglobulin complexes can enter pores with a high probability to some degree, and other proteins are prevented from entering pores as much as possible.

In the water-insoluble carrier used for the present invention, an average pore diameter of a porous carrier is preferably about 300 to about 10000 Å. The diameter of a pore is most often measured by a method of mercury porosimetry. However, in the case of a porous water-insoluble carrier used in the present invention, this method often could not be applied. As a criterion of the diameter of a pore, a molecular weight of the exclusion limit is preferably used. A molecular weight of the exclusion limit refers to a molecular weight of a molecule having the smallest molecular weight among molecules which cannot enter pores (i.e., which are excluded) in gel permeation chromatography (H. Hatano and T. Hanai, Experimental High Performance liquid Chromatography (Jikken Kosoku Ekitai Chromatography), Kagaku Dojin, 1988. A molecular weight of the exclusion limit is generally well investigated for globular proteins, dextran, polyethylene glycol, and the like. In the case of the porous water-insoluble carrier used in the present invention, a value obtained by using a globular protein is suitably used.

As a result of studying carriers having various molecular weights of the exclusion limit, the exclusion limit of a suitable carrier, which therefore has a pore diameter suitable for adsorbing immunoglobulins and/or immunoglobulin complexes, was found to be about 150,000 or more in molecular weight. More specifically, in the case where a carrier having a molecular weight of the exclusion limit of less than about 150,000 is used, an adsorbing and removing amount of immunoglobulins and/or immunoglobulin complexes is small, resulting in decreased practicability. Thus, a preferable molecular weight of the exclusion limit of the carrier used in the present invention is about 150,000 or more. On the other hand, in the case where a molecular weight of the exclusion limit exceeds about 5,000,000, no particular problems are caused as long as the plasma or the serum is used as the body fluid. However, macromolecules which have no interaction with a ligand have a tendency to block a binding site of a ligand, thereby substantially decreasing the effective ligand amount. Furthermore, in the case where the blood is used as the body fluid, when a molecular weight of the exclusion limit exceeds about 5,000,000, there is a tendency that a ratio at which the platelet adheres to a carrier increases. Thus, in the case where the adsorbent of the present invention is used in a hemocatharsis system of DHP (direct hemoperfusion) type, sufficient performance cannot necessarily be exhibited. On the other hand, in the case where a molecular weight of the exclusion limit is about 5,000,000 or less, no particular problems are caused even when carriers are used for any purpose. Thus, in order to use the adsorbent of the present invention for various purposes, a molecular weight of the exclusion limit is desirably about 5,000,000 or less. Accordingly, a more preferable molecular weight of the exclusion limit of the carrier used in the present invention is from about 150,000 to about 5,000,000.

Next, considering the adsorbing capacity per volume of an adsorbent, it is preferable that a carrier has a totally porous structure, rather than a surface porous structure, and a pore volume of 20% or more and a specific surface area of 3 $m^2/g$ or more. As a shape of a carrier, any shape such as a bead, a fiber, and/or a membrane (including a hollow thread) can be selected.

In order to immobilize a ligand, it is preferable that functional groups available for an immobilization reaction of a ligand are present on the surface of a carrier. Examples of the functional groups include a hydroxyl group, an amino group, an aldehyde group, a carboxyl group, a thiol group, a silanol group, an amide group, an epoxy group, a halogen group, a succinylimide group, and an acid anhydride group.

Next, as the carrier used in the present invention, any hard carrier and/or soft carrier can be used. In order to use a carrier as an adsorbent for an extracorporeal circulation treatment, it is important that when the carrier is packed into a column and the body fluid is passed through the column, the carrier does not cause clogging. Therefore, sufficient mechanical strength is required of the carrier. Thus, the carrier used in the present invention is preferably a hard carrier. In the present specification, a hard carrier refers to those in which, for example, in the case of a granular gel, where the gel is uniformly packed into a cylindrical column made of glass (inner diameter: 9 mm, column length: 150 mm) under the following conditions, and an aqueous fluid is passed through the column, the pressure loss $\Delta P$ and the flow rate of the aqueous fluid have a linear relationship up to a pressure of 0.3 $kg/cm^2$.

Figure 7:
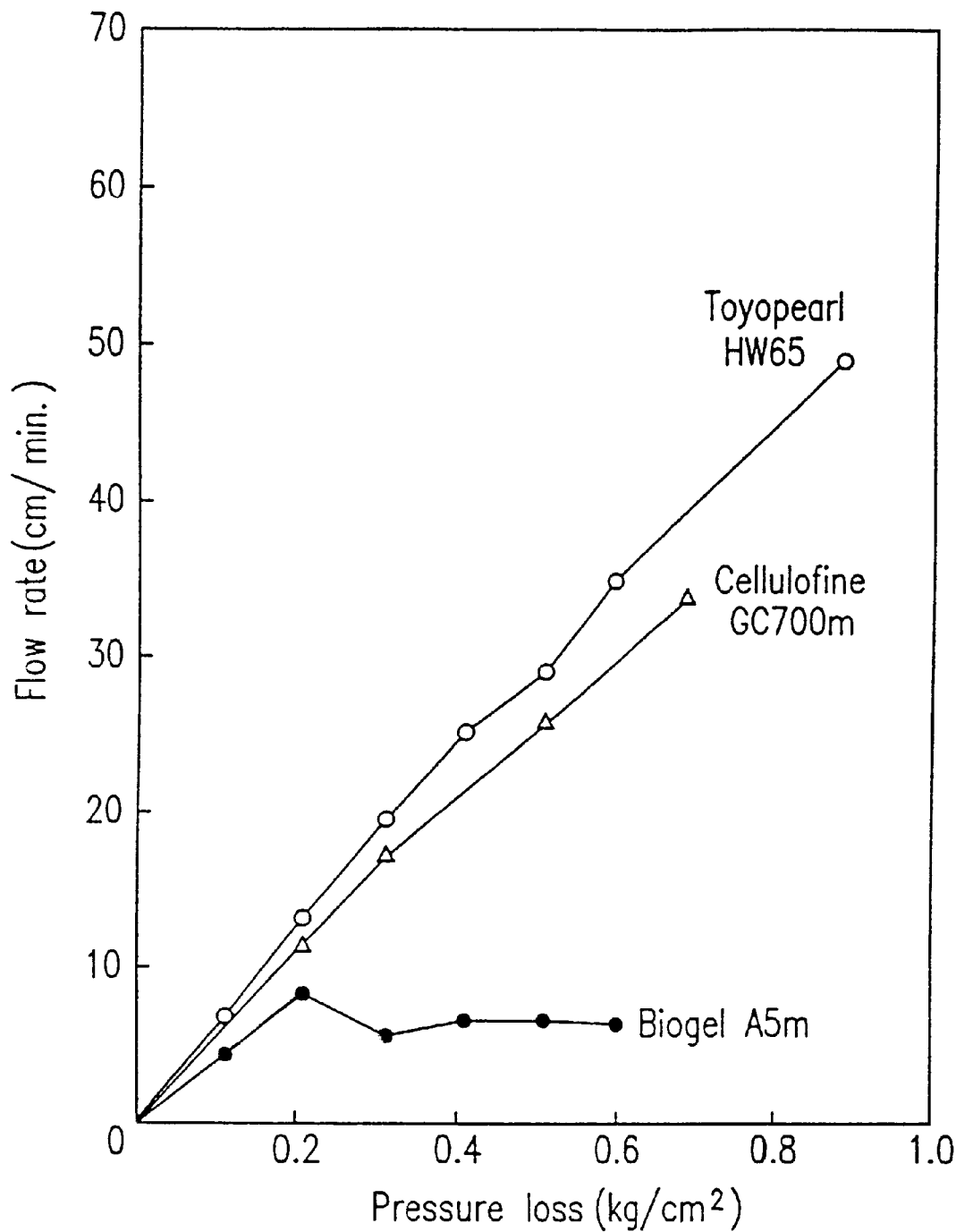
FIG. 7 is a graph showing results obtained by investigating the relationship between the flow rate and the pressure loss, by using three kinds of gels.

For example, an agarose gel (Biogel A-5m produced by Bio-Rad; particle diameter: 50 to 100 meshes), a vinyl type polymer gel (Toyopearl HW-65 produced by Toyo Soda Mfg. Co., Ltd.; particle diameter: 50 to 100 $\mu$m), and a cellulose gel (Cellulofine GC-700m produced by Chisso Corporation; particle diameter: 45 to 105 $\mu$m) were each uniformly packed into their own cylindrical column made of glass (inner diameter 9 mm; column length 150 mm) equipped with filters having a pore diameter of 15 $\mu$m at both ends. Water was passed through the column by a peristaltic pump, and the relationship between the flow rate and the pressure loss $\Delta P$ was obtained (FIG. 7). The flow rate (cm/min.) was plotted on an ordinate and the pressure loss ($kg/cm^2$) was plotted on an abscissa.

As can be seen in FIG. 7, ○, Δ, and ● represent Toyopearl HW-65, Cellulofine GC700m, and Biogel-A5m, respectively. As a result, it is understood that the flow rate of the aqueous fluid through Toyopearl HW-65 and Cellulofine GC-700m increases almost in proportion to the increase in a pressure, whereas Biogel A-5m results in compaction, and the flow rate does not increase with the increase in a pressure.

For immobilizing a peptide or a peptide derivative onto the above-mentioned carrier, in order to improve an adsorbing efficiently by minimizing a steric hindrance of a peptide or a peptide derivative and to suppress non-specific adsorption, a peptide or a peptide derivative is preferably immobilized onto a carrier via hydrophilic spacers. As the hydrophilic spacers, for example, derivatives of polyalkylene oxide in which both ends are replaced by carboxyl groups, amino groups, aldehyde groups, epoxy groups, or the like are preferably used.

Since an organic compound used as a peptide or a peptide derivative, and spacers introduced into the above-mentioned carrier are a relatively stable substance with a low molecular weight, there is a less stringent requirement for the immobilization reaction conditions, for example, compared with the case where a protein such as an enzyme and an antibody is immobilized. Thus, an immobilization method is not particularly limited. However, considering that an adsorbent may be used for extracorporeal circulation treatment and hemocatharsis, it is more preferable to apply an immobilization method in which peptides are not easily detached from an carrier during sterilization of the adsorbent or treatment. For example, there are (1) a method for allowing a carboxyl group of a carrier to be reacted with N-hydroxysuccinimide to replace the carboxyl group into a succinimideoxycarbonyl group, and allowing a peptide or a peptide derivative to be reacted at a portion of an amino group (active ester method), (2) a method for allowing a carboxyl group or an amino group of a peptide or a peptide derivative to be condensation-reacted with an amino group or a carboxyl group of a carrier in the presence of a condensation reagent such as dicyclohexylcarbodiimide (condensation method), and (3) a method for cross-linking a peptide or a peptide derivative to a carrier by using a compound having at least two functional groups such as glutaraldehyde (carrier cross-linking method). In order to reduce desorption and elution of peptides to a minimum, peptides are preferably bound to a carrier by a covalent bonding method.

There are various methods for adsorbing and removing immunoglobulins and/or immunoglobulin complexes in the body fluid by bringing a carrier on which a peptide functional group is immobilized into contact with the body fluid such as the blood and the plasma. Representative examples include (1) a method including the steps of taking out the body fluid, storing it in a bag, mixing the body fluid with an adsorbent to adsorb and remove immunoglobulins and/or immunoglobulin complexes, and filtering off the adsorbent, thereby obtaining body fluid from which immunoglobulins and/or immunoglobulin complexes has been removed, and (2) a method for charging an adsorbent into a vessel having an inlet and an outlet for the body fluid and equipped with a filter at the outlet, which passes the body fluid but does not pass the adsorbent, and flowing the body fluid through the vessel, and the like. Any method for adsorbing and removing immunoglobulins and/or immunoglobulin complexes may be used. However, the latter method is easy to operate, and furthermore, the vessel can be incorporated into an extracorporeal circulation circuit, whereby immunoglobulins and/or immunoglobulin complexes can be removed efficiently from the body fluid of a patient on line. Thus, the adsorbent of the present invention is suitable for this method.

Next, a device for adsorbing immunoglobulins and/or immunoglobulin complexes of the present invention using an adsorbent for adsorbing immunoglobulins and/or immunoglobulin complexes will be described with reference to its schematic cross-sectional view.

Figure 6:
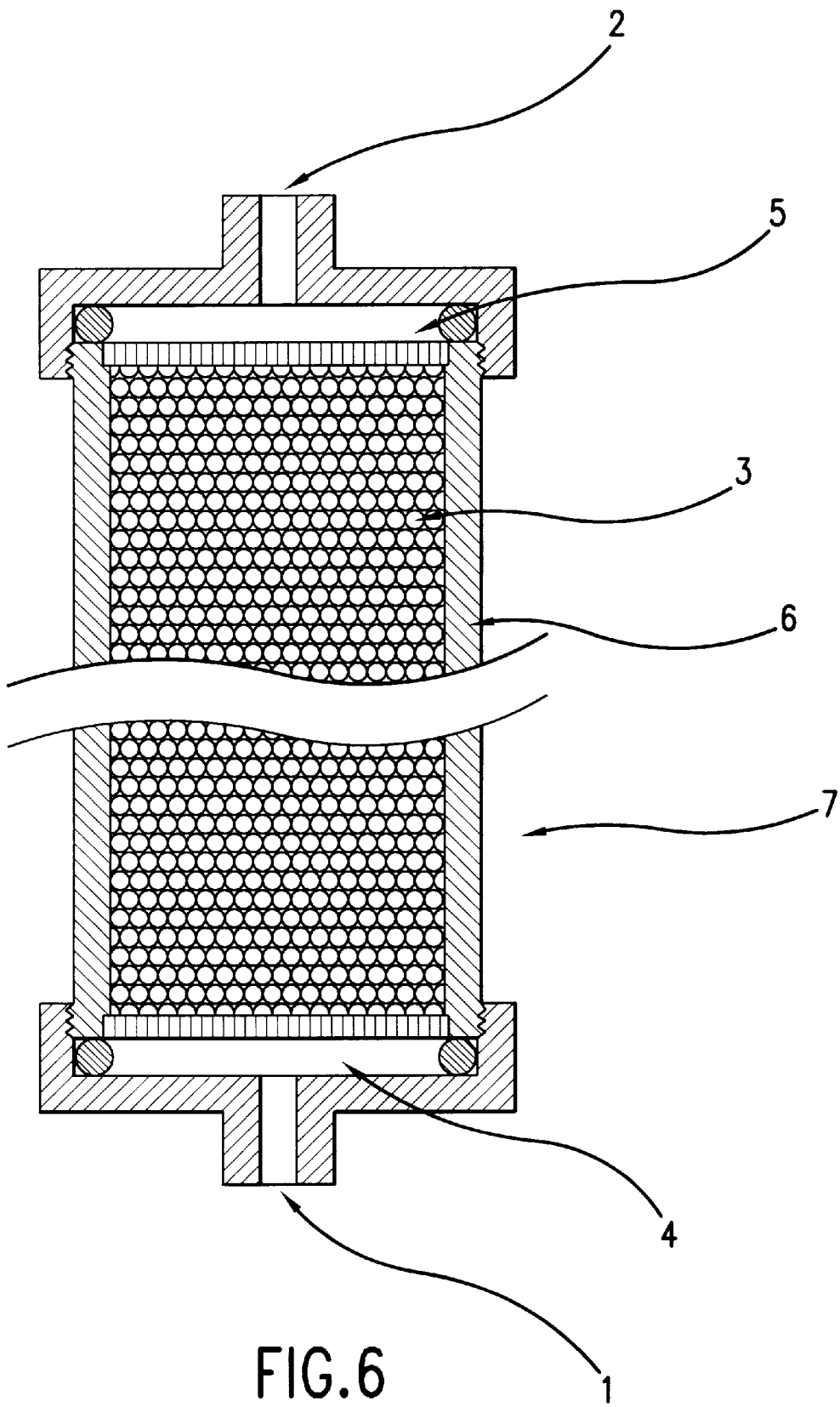
FIG. 6 is a schematic cross-sectional diagram of one example of a device for adsorbing immunoglobulins and/or immunoglobulin complexes of the present invention.

A vessel 7 shown in FIG. 6 includes an inlet or outlet 1 for a solution, an outlet or inlet 2 for a solution, an immunoglobulin and/or immunoglobulin complex adsorbent 3 of the present invention, effluent preventing means 4 and 5 for preventing the out-flow of the adsorbent, which allows a solution and a component contained therein to pass therethrough but does not allow the adsorbent to pass therethrough, and a column 6. The shape and material for this vessel are not particularly limited. However, for example, a cylindrical vessel with a capacity of about 20 to about 400 ml and a diameter of about 2 to about 10 cm is preferably used.

The present invention will be described in more detail by way of the following examples. It should be noted that the present invention is not limited to the following examples.

EXAMPLES

Example 1

Chemical Synthesis of a Peptide and Immobilization of the Peptide Onto Sepharose Chemical Synthesis of a Peptide Synthesis of a peptide having a sequence consisting of 57 residues of domain C3 of protein G with cysteine added to an N-terminus was conducted as follows by a solid phase synthesis method, using a Peptide Synthesizer Model 4170 (manufactured by Pharmacia LKB). Using 0.1 mmol of Fmoc-glutamine NovaSyn KA (produced by Pharmacia LKB) which is a support to which glutamine corresponding to the C-terminus is bound, a deprotection reaction and a condensation reaction are repeated in accordance with a synthesis program input to the Peptide Synthesizer, whereby a peptide chain was successively elongated by addition to the N-terminus. More specifically, the following process steps were repeated: A 9-fluorenylmethyloxycarbonyl group (hereinafter, referred to as "Fmoc") which is a protecting group of an α-amino group of the amino acid is removed by piperidine, the peptide chain was washed with N,N-dimethylformamide (hereinafter, referred to as "DMF"), a condensation reaction was conducted by using 2-(1H-benzotriazole-1-yl)-1,1,3,3-tetramethyluroniumtetrafluorophosphate (hereinafter, referred to as "HBTU" and N,N-diisopropylethylamine (hereinafter, referred to as "DIPEA"), and the peptide chain was washed with DMF. As amino acids, Fmoc-L-Ala, Fmoc-L-Asn(Trt), Fmoc-L-Asp(OtBu), Fmoc-L-Cys(Trt), Fmoc-L-Gln(Trt), Fmoc-L-Glu(OtBu), Fmoc-L-Gly, Fmoc-L-Ile, Fmoc-L-Leu, Fmoc-L-Lys(Boc), Fmoc-L-Phe, Fmoc-L-Thr. (tBu), Fmoc-L-Trp, Fmoc-L-Tyr(tBu), and Fmoc-L-Val were used. These amino acids (0.5 mmol) were used in a vial. The amount of amino acids used is about 5 times the amount of moles of a substrate which is used. (Herein, Trt, OtBu, Boc, and tBu represent a trityl group, an o-tertiary butyl ester, a tertiary butyl oxycarbonyl group, and a tertiary butyl group, respectively.)

Deprotection Reaction and Cleaving Off of a Peptide Chain

After a reaction operation was completed for all the amino acids, the resultant support was washed with tert-amyl alcohol, acetic acid, and diethyl ether, successively, on a glass filter with a 3G-3 pore. Then, the support was dried in a vacuum, whereby a dry support was obtained. In a vial, 20 ml of TFA, 260 μl of 1,2-ethanedithiol, and 780 μl of anisole were added to 1 g of the obtained support, and the mixture was stirred at room temperature for 1.5 hours. Thereafter, the mixture was separated off the support by filtration through the glass filter with a 3G-3 pore. The resultant filtrate was condensed at 35° C. under reduced pressure. To the condensed filtrate, previously cooled absolute diethyl ether was added, and the resultant mixture was stirred until no absolute diethyl ether is precipitated. Then, the mixture was centrifuged, and a crude peptide precipitate was collected. Furthermore, the crude peptide was washed several times with absolute diethyl ether, and thereafter, dried under a reduced pressured, whereby a crude purified peptide of interest was obtained.

Purification of a Peptide

The crude purified peptide thus obtained was dissolved in 0.1% TFA, and the solution was filtered through a 0.2 μm membrane filter. The filtrate thus obtained was subjected to high-performance liquid chromatography (HPLC). For HPLC, a Model LC-10A system (manufactured by Shimadzu Corporation) was used, and as a column, a reverse phase type pBondasphere C18 (manufactured by Nihon Millipore Waters Ltd.) was used. For a mobile phase, using 0.1% TFA aqueous solution as A solution and 80% (v/v) acetonitrile/water containing 0.1% TFA as B solution, the column was eluted by a linear concentration gradient from A solution to B solution. Fractions corresponding to a peptide at the peak of the obtained chromatogram were collected. Collection was repeated several times, and the fractions were lyophilized, whereby a purified peptide was obtained. The peptide thus obtained was analyzed by gas-phase protein sequencer model 477 (manufactured by Applied Biosystems Co. Ltd. ), and amino acid analysis using a Hitachi custom ion exchange resin. Thus, it was confirmed that a peptide having the amino acid sequence represented by ID SEQ NO: 2 was obtained.

Immobilization of a Peptide Onto Sepharose

The above-mentioned peptide was immobilized onto porous Sepharose, whereby an adsorbent was produced as follows. As Sepharose, Thiopropyl Sepharose 6B (produced by Pharmacia LKB) was used. To 50 mg of Thiopropyl Sepharose 6B, 50 ml of distilled water was added, and the mixture was allowed to stand at room temperature for 15 minutes, whereby the resin was allowed to swell. Then, the distilled water was removed and replaced by 0.1 M Tris hydrochloride (pH 7.5) coupling buffer containing 0.5 M of NaCl.

On the other hand, 4 mg of the above-mentioned purified peptide was dissolved in 400 μl of 0.1 M Tris hydrochloride (pH 7.5) coupling buffer containing 0.5 M of NaCl, and 40 mg of the above-mentioned Thiopropyl Sepharose 6D was added to the resultant solution. The mixture was stirred at 4° C. for 12 hours, whereby an adsorbent with the purified peptide immobilized thereon was obtained. Furthermore, the resultant adsorbent with the peptide immobilized thereon was filtered by suction, and the content of the peptide in the filtrate was quantitated by an absolute calibration curve method, using HPLC. Thus, a ratio of the peptide immobilized onto the carrier was obtained. The adsorbent with the peptide immobilized thereon was thoroughly washed with 10 mM of phosphate buffer (pH 7.2) containing 150 mM of NaCl, and filtered by suction, whereby a peptide-Sepharose adsorbent of interest was obtained.

Example 2

Evaluation of Adsorbing Capacity of an Adsorbent with a Peptide Immobilized Thereon Test 1

The adsorbent produced in the above-mentioned Example 1 was evaluated for adsorbing capacity of thermally coagulated complexes (model of an immune complex) in the blood, by using the serum of a healthy subject. Fifty microliters (one volume) of the above-mentioned adsorbent was collected in a vial, and 150 μl (three volumes) of the serum of a healthy subject containing 20 μg/ml of thermally coagulated complexes (see M. Makino, Clinical Immunology, Vol. 18, pp. 111–119 (1986)) was added to the adsorbent, and the serum and the adsorbent were incubated with shaking at 37° C. for 2 hours. Furthermore, as a control, 150 μl (3 volumes) of the serum of a healthy subject containing 20 μg/ml of thermally coagulated complexes to 50 μl (1 volume) of an untreated support, and the serum and the support were incubated with shaking at 37° C. for 2 hours. Thereafter, these suspensions were centrifuged at 5,000 rpm for one minute, and the amount of the complexes in the supernatants were measured by an extracorporeal diagnostic kit "FRELISA Clq-CIC" manufactured by Fujirebio Inc.

The results are shown in Table 1. The adsorption ratio of the thermally coagulated complexes was represented by an adsorption ratio (%) calculated from a value of the control serum by the following equation. Furthermore, each adsorbing capacity of immunoglobulins (IgG, IgA, IgM) was quantitated by an extracorporeal diagnostic medical product "N-Assay TIA" measurement kit commercially available from Nittobo Co., Ltd. The results are shown in Table 2. Furthermore, IgG subclasses ($IgG_1$, $IgG_2$, $IgG_3$, $IgG_4$) were quantitated by a measurement kit using an immune diffusion (SRID) method commercially available from Bindingsite. The results are shown in Table 3.

$$\text{Adsorption removal ratio (\%)} = \frac{\text{Complex concentration in the control solution} - \text{Complex concentration in the test solution}}{\text{Complex concentration in the control solution}} \times 100$$

TABLE 1

| Adsorbent | Immobilized amount (mg/ml) | Adsorption ratio of thermally coagulated complexes (%) |
|---|---|---|
| non-immobilized thiopropyl carrier | 0.0 | 0.0 |
| Thiopropyl carrier with a ligand immobilized thereon | 0.8 | 41.7 |

TABLE 2

| Adsorbent | Immobilized amount (mg/ml) | Adsorption ratio of immunoglobulins (%) | | |
|---|---|---|---|---|
| | | IgG | IgA | IgM |
| Non-immobilized thiopropyl carrier | 0.0 | 0.0 | 0.0 | 0.0 |
| Thiopropyl carrier with a ligand immobilized thereon | 0.8 | 83.4 | 0.0 | 2.7 |

TABLE 3

| Adsorbent | Immobilized amount (mg/ml) | Adsorption ratio of IgG subclasses (%) | | | |
|---|---|---|---|---|---|
| | | $IgG_1$ | $IgG_2$ | $IgG_3$ | $IgG_4$ |
| Non-immobilized thiopropyl carrier | 0.0 | 0.0 | 0.0 | 0.0 | 0.0 |
| Thiopropyl carrier with a ligand immobilized thereon | 0.8 | 93.2 | 78.9 | 63.2 | 65.7 |

From the above results, it was discovered that the use of the adsorbent of the present invention enables IgG which is a component of immune complexes and immune complexes to be selectively adsorbed and removed, and enables $IgG_3$ which is not adsorbed by protein A to be adsorbed and removed.

Test 2

The above-mentioned adsorbent was evaluated for adsorbing capacity of circulating immune complexes in the blood by using the serum of a patient suffering from rheumatism. Fifty microliters (one volume) of the above-mentioned adsorbent was collected in a vial, and 150 μl (three volumes) of the serum of a patient suffering from rheumatism was added to the adsorbent, and the serum and the adsorbent were incubated with shaking at 37° C. for 2 hours. Furthermore, as a control, 150 μl (3 volumes) of the serum of a patient suffering from rheumatism was added to 50 μl (1 volume) of an untreated support, and the serum and the support were incubated with shaking at 37° C. for 2 hours. Thereafter, these suspensions were centrifuged at 5,000 rpm for one minute, and the amount of the complexes in the supernatant was measured by the method described in Test 1. The results are shown in Table 4 together with the adsorption ratio (%) calculated from a value of the control serum. Furthermore, each adsorbing capacity of immunoglobulins (IgG, IgA, IgM) was quantitated by the above-mentioned method. The results are shown in Table 5.

TABLE 4

| Adsorbent | Immobilized amount (mg/ml) | Adsorption ratio of immune complexes (%) |
|---|---|---|
| non-immobilized thiopropyl carrier | 0.0 | 0.0 |
| Thiopropyl carrier with a ligand immobilized thereon | 0.8 | 29.3 |

TABLE 5

| | Immobilized amount (mg/ml) | Adsorption ratio of immunoglobin (%) | | |
|---|---|---|---|---|
| Adsorbent | | IgG | IgA | IgM |
| Non-immobilized thiopropyl carrier | 0.0 | 0.0 | 0.0 | 0.0 |
| Thiopropyl carrier with a ligand immobilized thereon | 0.8 | 21.1 | 0.0 | 2.7 |

From Tables 4 and 5, it was discovered that the use of the adsorbent of the present invention enables IgG which is a component of immune complexes in the blood of a patient suffering from rheumatism and immune complexes to be selectively adsorbed and removed.

Example 3
High-pressure Vapor Sterilization Stability of an Adsorbent with a Peptide Immobilized Thereon Autoclave Treatment of an Adsorbent Fifty microliters of the adsorbent produced in Example 1 was suspended in 1 ml of 10 mM phosphate buffer (pH 7.2) containing 150 mM of NaCl, and the resultant suspension was heated under a high pressure at 121° C. for 20 minutes in an autoclave sterilizer.

Evaluation of Adsorbing Capacity of an Adsorbent Subjected to an Autoclave Treatment The serum was suspended in the same way as in Example 2, using the adsorbent obtained in Example 1 and the above-mentioned adsorbent treated by autoclave sterilization. The concentrations of complexes and immunoglobulins in the obtained supernatant were measured to calculate an adsorption and removal ratio. The results are shown in Tables 6 and 7.

TABLE 6

| Adsorbent | Immobilized amount (mg/ml) | Adsorption ratio of immune complexes (%) |
|---|---|---|
| non-immobilized thiopropyl carrier | 0.0 | 0.0 |
| Thiopropyl carrier with a ligand immobilized thereon | 2.4 | 78.3 |
| Carrier with a ligand immobilized thereon treated at 121° C. for 20 minutes | 2.4 | 12.5 |

TABLE 7

| | Immobilized amount (mg/ml) | Adsorption ratio of immunoglobulin (%) | | |
|---|---|---|---|---|
| Adsorbent | | IgG | IgA | IgM |
| Non-immobilized thiopropyl carrier | 0.0 | 0.0 | 0.0 | 0.0 |
| Thiopropyl carrier with a ligand immobilized thereon | 2.4 | 58.8 | 0.0 | 1.8 |
| Carrier with a ligand immobilized thereon treated at 121° C. for 20 minutes | 2.4 | 8.8 | | |

From the above-mentioned test results, it was found that the adsorbent with the peptide immobilized thereon of the present invention has its adsorption removal capacity decreased by an autoclave sterilization treatment, while maintaining an adsorption removal capacity with respect to complexes and IgG.

Example 4
Production of a Peptide Derivative MK3P47 Peptide

DNA (DNA sequence represented by SEQ ID NO: 5) encoding MK3P47 peptide represented by SEQ ID NO: 4 was synthesized. This DNA is designed so as to be connected by utilizing each restriction enzyme site (NdeI on a 5' side; HindIII on a 3' side) of a pUCNT vector (Japanese Laid-open Publication No. 4-212692).

DNA having the above-mentioned sequence was connected to a pUCNT vector cleaved by digestion with restriction enzymes NdeI and HindIII (produced by Takara Shuzo Co., Ltd.) by using DNA Ligation Kit Ver. 2 produced by Takara Shuzo Co., Ltd. in accordance with a procedure, whereby a pUCNTMK3P47 vector (FIG. 1) was produced.

The pUCNTMK3P47 vector DNA was introduced into E. coli HB101 strain (available from Funakoshi) by using a known method, and a transformant was selected based on resistance with respect to antibiotic ampicillin as an index. Furthermore, plasmid DNA was extracted from this transformant by a conventional method and determined for its sequence, whereby it was confirmed that the pUCNTMK3P47 vector has a DNA sequence as designed. Next, the transformant was cultured with shaking in 6 L of L-broth (5 g/L of NaCl, 10 g/L of bactotrypsin, 5 g/L of yeast extract) at 37° C. for 20 hours, and cultures were centrifuged (at 4° C. and 6000 rpm for 20 minutes, using a Hitachi RPR9-2 rotor) to collect the cells. The pellets thus obtained were suspended in 300 ml of a TE buffer (20 mM of Tris-HCl, 1 mM of EDTA: pH 7.5), and the resultant suspension was subjected to ultrasonication disruption (3 times (each for 6 minutes) in the ice, using BRANSON 250). Then, the suspension was centrifuged (at 4° C. and 15000 rpm for 20 minutes, using a Hitachi RPR16 rotor), and a supernatant was collected. The supernatant thus obtained was heated at 70° C. for 10 minutes, centrifuged (at 4° C. and 15000 rpm for 20 minutes, using a Hitachi RPR16 rotor), and 300 ml of a supernatant was collected. MK3P47 peptide was purified from the supernatant thus obtained, by using HPLC chromatography (column: Waters PBONDA-SPHERE 5µ C18 300 A 19.0×150 mm) as follows. First, 40 ml of 0.1% TFA solution was passed through the column at a flow rate of 5 ml/min to activate the column, and 300 ml of a sample was passed through the column at the same flow rate. The column was washed with 200 ml of 0.1% TFA+

14% acetonitrile solution. Then, MK3P47 peptide derivative of interest was eluted from the column by using 200 ml of 0.1% TFA+40% acetonitrile solution, whereby fractions containing MK3P47 peptide were collected. The fractions were concentrated to 100 ml by an evaporator and lyophilized, whereby 1.2 g of MK3P47 peptide was collected as a high purity purified sample. This sample was used for various studies.

Example 5
Production of a Peptide Derivative MP47K3 Peptide

DNA represented by SEQ ID NO: 7 encoding MP47K3 peptide represented by SEQ ID NO: 6 was synthesized by using the method similar to that of Example 4, and a pUCNTMP47K3 vector was produced by using the DNA and a pUCNT vector. Then, the vector was transformed into *E. coli*. The transformant thus obtained was cultured (6 L), and the MP47K3 peptide of interest was purified, whereby 600 mg of a high purity sample was obtained.

Example 6
Production of a Peptide Derivative MP47 Peptide

DNA represented by SEQ ID NO: 9 encoding MP47 peptide represented by SEQ ID NO: 8 was synthesized by using the method similar to that of Example 4, and a pUCNTMP47 vector was produced by using the DNA and a pUCNT vector. Then, the vector was transformed into *E. coli*. The transformant thus obtained was cultured (6 L), and the MP47 peptide of interest was purified, whereby 500 mg of a high purity sample was obtained.

Example 7
Production of a Peptide Derivative MP47C Peptide

DNA represented by SEQ ID NO: 11 encoding MP47C peptide represented by SEQ ID NO: 10 was synthesized by using the method similar to that of Example 4, and a pUCNTMP47 vector was produced by using the DNA and a pUCNT vector. Then, the vector was transformed into *E. coli*. The transformant thus obtained was cultured (6 L), and the MP47C peptide of interest was purified, whereby 1.3 g of a high purity sample was obtained.

Example 8
Production of MK3G56 Peptide for Comparison

DNA represented by SEQ ID NO: 13 encoding MK3G56 peptide represented by SEQ ID NO: 12 was synthesized by using the method similar to that of Example 4, and a pUCNTMK3G56 vector was produced by using the DNA and a pUCNT vector. Then, the vector was transformed into *E. coli*. The transformant thus obtained was cultured (6 L), and the MK3G56 peptide of interest was purified, whereby 1.0 g of a high purity sample was obtained.

Example 9
Production of a Peptide Derivative MK3-7M Peptide

DNA represented by SEQ ID NO: 15 encoding MK3-7M peptide represented by SEQ ID NO: 14 was synthesized by using the method similar to that of Example 4, and a pUCNTMK3-7M vector was produced by using the DNA and a pUCNT vector. Then, the vector was transformed into *E. coli*. The transformant thus obtained was cultured (6 L), and the MK3-7M peptide of interest was purified, whereby 800 mg of a high purity sample was obtained.

Example 10
Production of MG56 Peptide for Comparison

DNA represented by SEQ ID NO: 17 encoding MG56 peptide represented by SEQ ID NO: 16 was synthesized by using the method similar to that of Example 4, and a pUCNTMG56 vector was produced by using the DNA and a PUCNT vector. Then, the vector was transformed into *E. coli*. The transformant thus obtained was cultured (6 L), and the MG56 peptide of interest was purified, whereby 400 mg of a high purity sample was obtained.

Example 11
Drug Denaturation Curve Analysis of a Peptide

Figure 2:
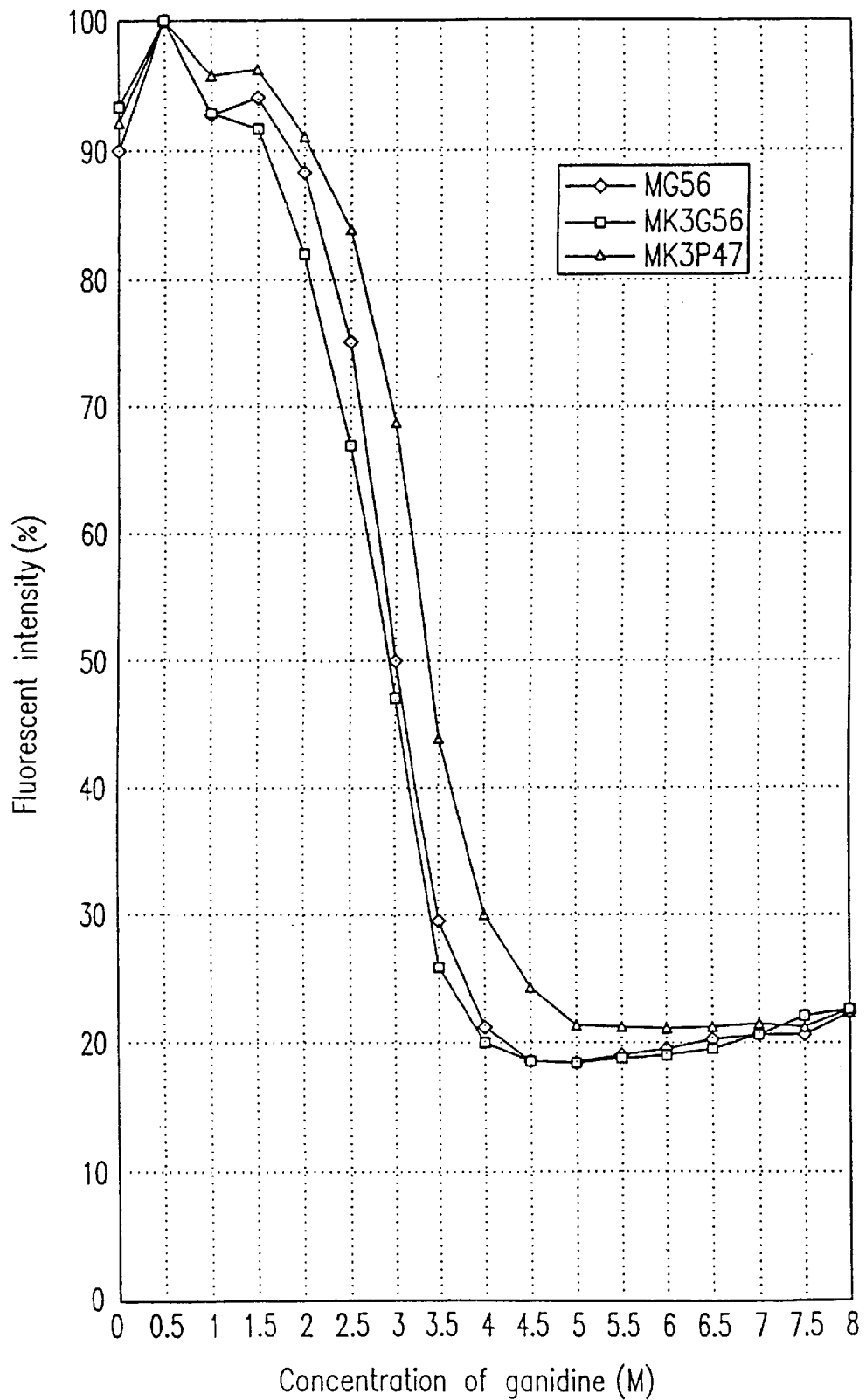
FIG. 2 shows denaturation curves of MG56, MK3G56, and MK3P47 peptides obtained by using guanidine hydrochloride.
Figure 3:
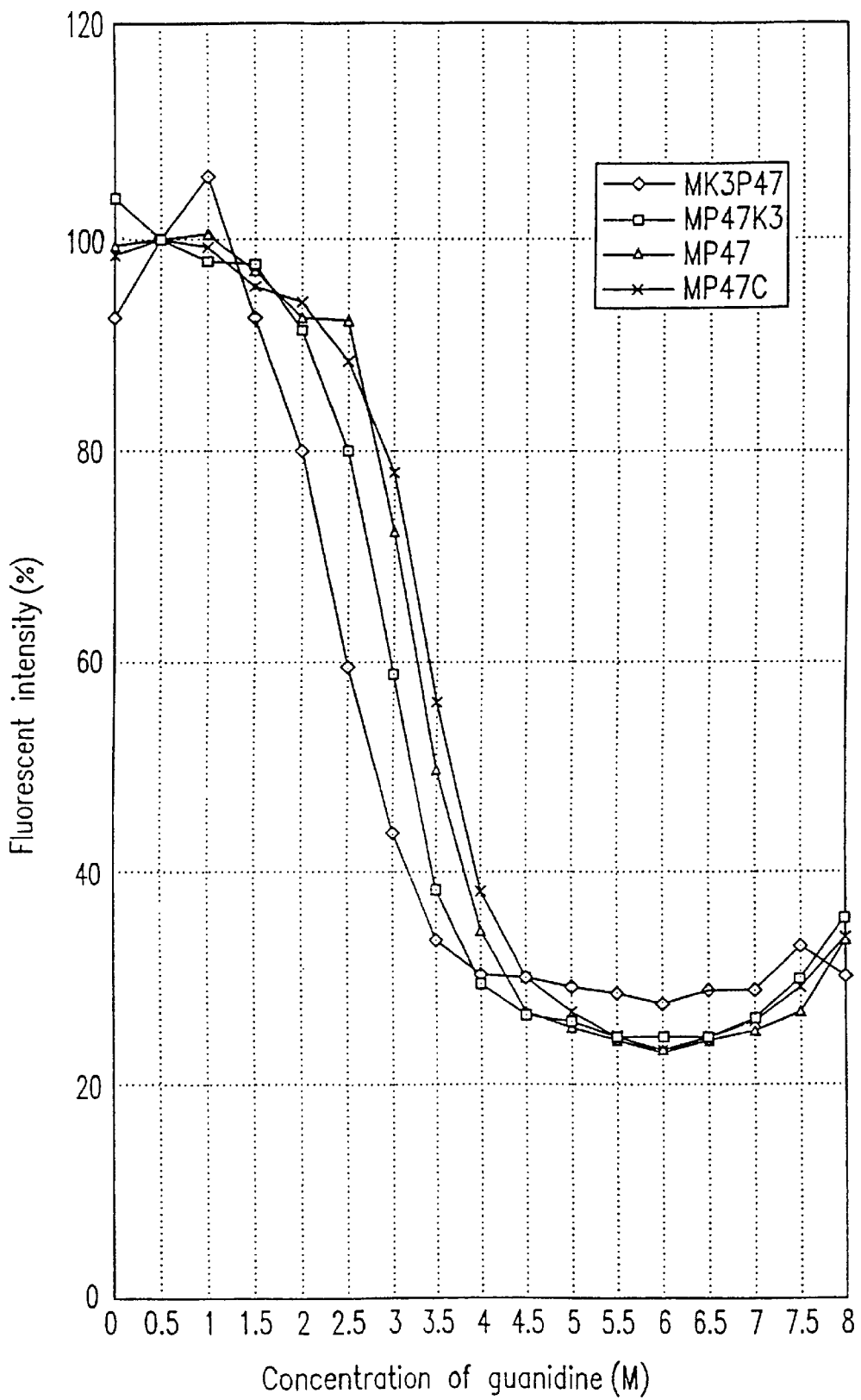
FIG. 3 shows denaturation curves of MK3P47, MP47K3, MP47, and MP47C peptides obtained by using guanidine hydrochloride.

First, 1 mg/ml of an aqueous solution of each peptide obtained in Examples 4 to 8 and Example 10 was diluted to 10 $\mu$g/ml by 0 to 8 M of a guanidine hydrochloride solution (at 30° C.), and a fluorescent intensity at EM 340 nm (excited at EX 278 nm) was measured by F-2000 type spectrofluorometer manufactured by Hitachi, Ltd. The results are shown in FIGS. 2 and 3. The fluorescent intensity (%) was plotted on an ordinate, and the concentration of guanidine (M) was plotted on an abscissa. In FIG. 2, ◊, □, Δ, and × represent a MG56 peptide, MK3G56 peptide, and MK3P47 peptide, respectively. In FIG. 3, ◊, □, Δ, and × represent a MK3P47 peptide, MP47K3 peptide, MP47 peptide, and MP47C peptide, respectively. Consequently, as shown in FIGS. 2 and 3, when the height of denaturation concentration of each peptide was compared, a relationship MP47C>MP47>MP47K3>MK3P47>MG56>MK3G56 was obtained.

Example 12
Measurement of a Thermal Denaturation Point of a Peptide

Figure 4:
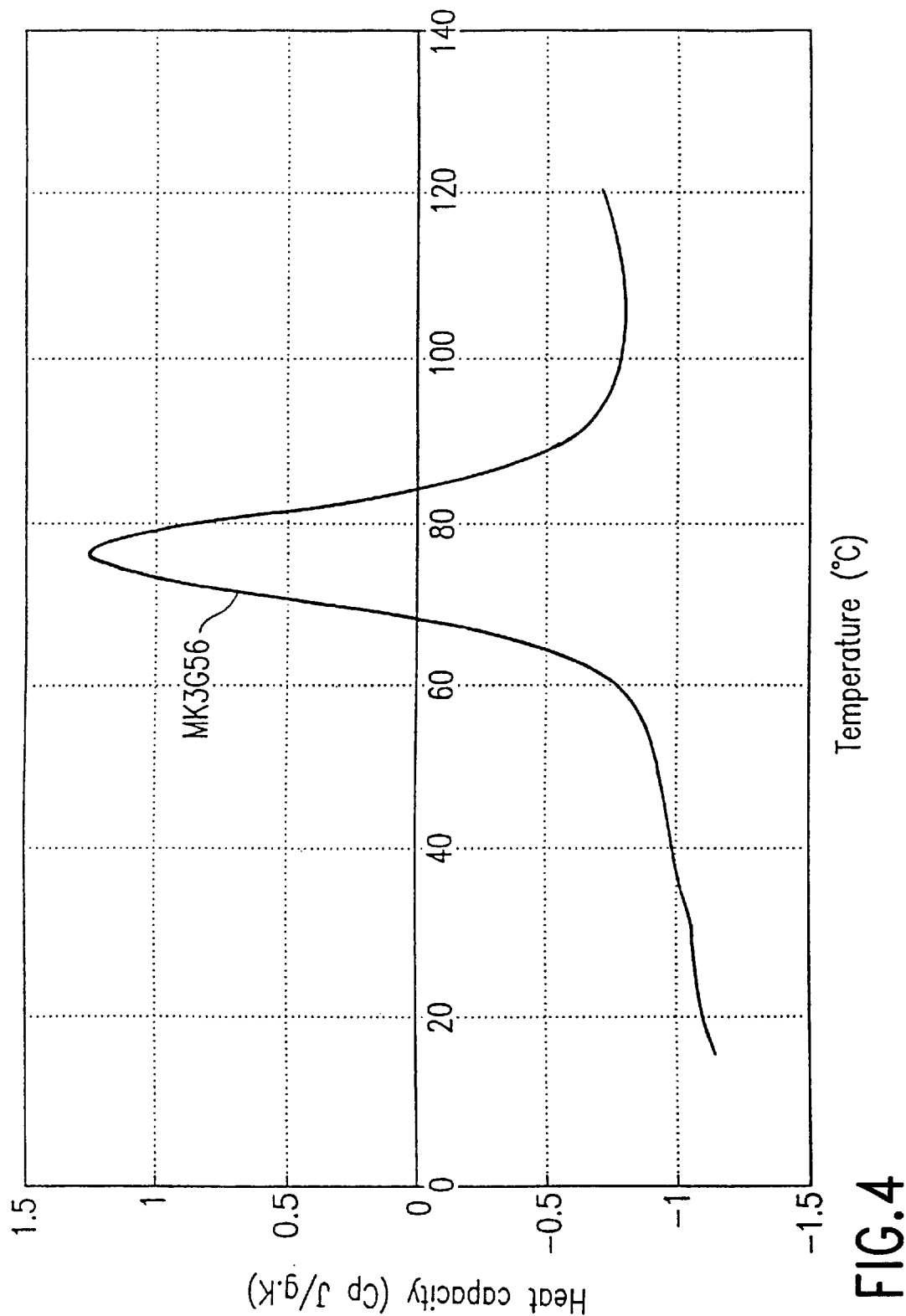
FIG. 4 shows excess heat capacity curves of MK3G56 peptide obtained by thermal denaturation with DASM-4.
Figure 5:
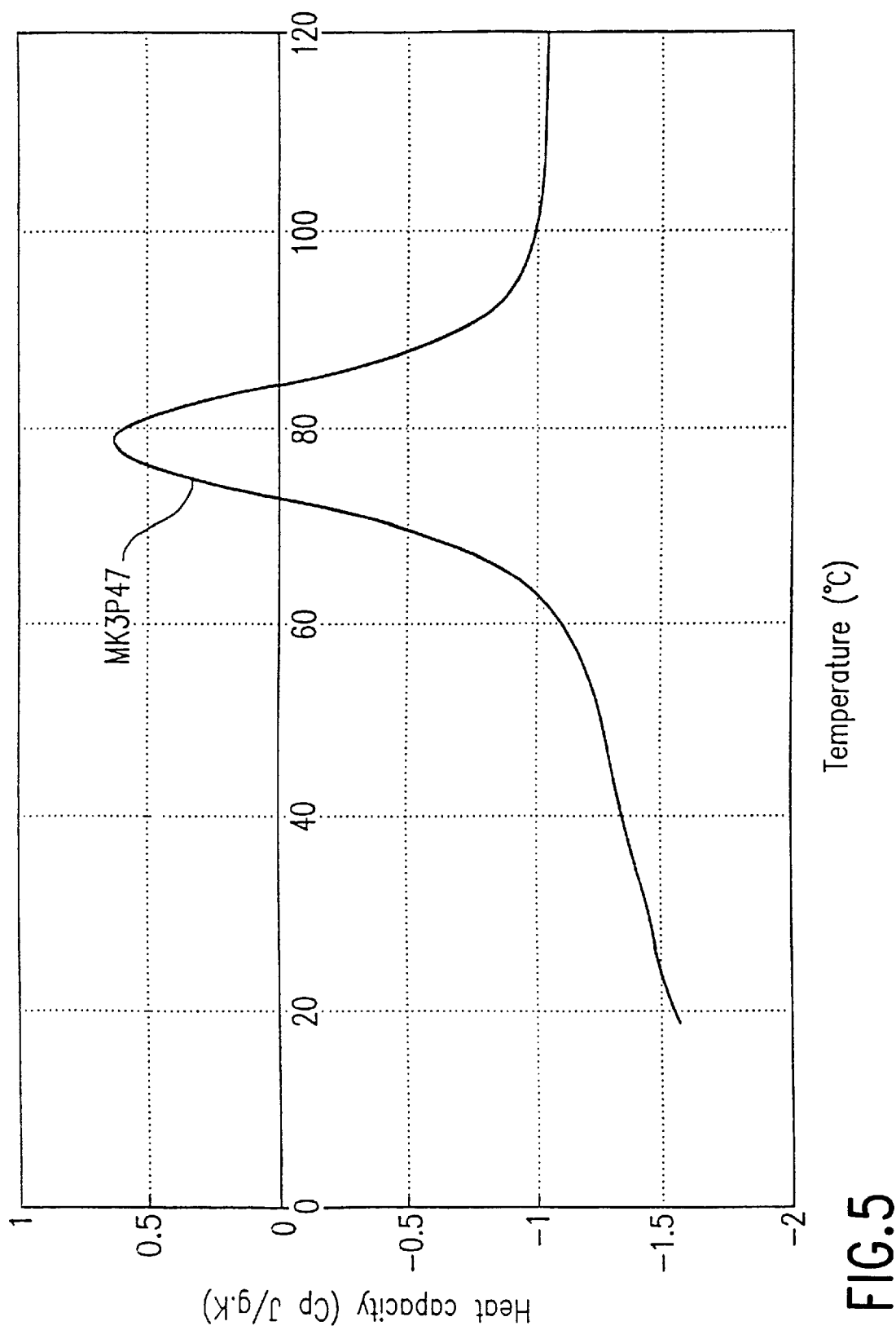
FIG. 5 shows excess heat capacity curves of MK3P47 peptide obtained by thermal denaturation with DASM-4.

MK3G56 peptide and MK3P47 peptide were measured for a thermal denaturation point by an adiabatic type differential scanning calorimeter DASM-4 (manufactured by Mashpriborintorg in Russia: Japanese agent, Shinkurikou Kabushikikaisha) with reference to a method described in Protein, Nucleic acid, Enzyme, Vol. 33, No. 4 (1988) pp. 337–347. The results are shown in FIGS. 4 and 5. The heat capacity (Cp J/g.k) was plotted on an ordinate, and the temperature (° C.) was plotted on an abscissa. As shown in FIG. 4 (MK3G56) and FIG. 5 (MK3P47), the thermal denaturation point of the MK3G56 peptide was 76.3° C., whereas that of the MK3P47 peptide was 78.1° C. This shows that an amino acid Pro at position 47 in SEQ ID NO: 3 apparently improves thermal stability.

Example 13
Immobilization and γ-ray Sterilization Stability of K3P47 Peptide

Water was added to 90 ml of GCL2000m (produced by Chisso Corporation, a molecular weight of the exclusion limit of a globular protein: 3,000,000) which is a cellulose type porous hard gel so that a total volume became 180 ml. Thereafter, 60 ml of 2 M sodium hydroxide was added to the mixture, and the resultant mixture was heated to 40° C. Then, 21 ml of epichlorohydrin was added to the mixture, and the mixture was allowed to react at 40° C. for one hour with stirring. After the completion of the reaction, the reaction product was thoroughly washed with water to obtain an epoxy activated gel.

The epoxy activated gel was suction-dried (aspirated by an aspirator on a glass filter G3 for 15 minutes). One gram of epoxy activated gel was suspended in 2.7 ml of a borate buffer (pH 10.0) (8.74 ml of 0.1 N aqueous sodium hydroxide was added to 10 ml of an aqueous solution of 0.1 M sodium tetraborate and 0.1 M potassium chloride, and water was added to the mixture so that a total volume became 20 ml), and 10 mg of MK3P47 peptide (SEQ ID NO: 4) was added to the suspension. The resultant suspension was allowed to react at 40° C. for 60 hours with stirring.

The supernatants of the reactant before and after the reaction were 2-fold diluted, respectively. Then, 100 μl of a BCA measurement reagent (produced by Pierce) was added to each 10 μl of the diluted supernatants, then the supernatants were incubated at 37° C. for 30 minutes. Thereafter, the absorbance at λ=550 nm was measured. Calibration was conducted and the concentration of the peptide and the immobilized amount thereof before and after the reaction were calculated. As a result, the reaction yield of the peptide with respect to the gel was 34%, and the immobilized amount thereof was 2.1 mg per 1 ml of gel.

The synthetic adsorbent with the peptide immobilized thereon was washed with a sufficient amount of saline to obtain adsorbent GCL2000mMK3P47.

Furthermore, a part of the synthesized adsorbent GCL2000mMK3P47 was subjected to γ-ray sterilization (25 kGy) while being suspended in a saline, thereby obtaining adsorbent γGCL200mMK3P47 subjected to γ-ray sterilization. (Hereinafter, an adsorbent subjected to γ-ray sterilization will be represented with γ.)

Then, 300 μl of the human serum containing 20 μg/ml of thermally coagulated immunoglobulin complexes (hereinafter, referred to as "Model IC") was added to 100 μl of the adsorbent GCL200mMK3P47 or γGCL2000mMK3P47 thus obtained, and the mixture was shaken at 37° C. for 2 hours. The supernatant of the serum was collected by centrifugation, and the concentrations of immunoglobulins (hereinafter, referred to as "IgG") and IC were measured to calculate an adsorption ratio. The concentration of IgG was measured by an extracorporeal diagnostic medical product "N-Assay TIA" measurement kit available from Nittobo, and the concentration of IC was measured by an enzyme immunoassay Flerizer Clq-CIC, manufactured by Fujirebio Inc. in accordance with a manual attached thereto. The results are as shown in Table 8. Specifically, the GCL2000mMK3P47, using as a ligand, recombinant MK3P47 peptide in which Asp at position 47 of the C3 peptide was replaced by Pro, and Lys-Lys-Lys- was added to the N-terminus as a functional group for immobilization to a carrier, showed high adsorbing capacity with respect to IC and IgG, and the adsorbing capacity hardly decreased even after subjected to γ-ray sterilization.

Example 14
Immobilization and γ-ray Sterilization Stability of MK3G56 Peptide An adsorbent GCL2000mMK3G56 and an adsorbent γGCL2000mMK3G56 were obtained in the same way as in Example 13, except that MK3G56 peptide obtained in Example 8 was used. The reaction yield of the peptide with respect to a gel was 40%, and the immobilized amount thereof was 2.5 mg per 1 ml of gel.

The IgG adsorption ratio and the IC adsorption ratio of the GCL200mMK3G56 or γGCL200mMK3G56 thus obtained are as shown in Table 8. The GCL2000mMK3G56, using as a carrier recombinant MK3G56 peptide in which Lys-Lys-Lys- was added to the N-terminus of the C3 peptide as a function group for immobilization to a carrier, exhibited a relatively high adsorption ratio with respect to IgG and IC. However, the GCL2000mMK3G56 lost most of its adsorbing capacity after being subjected to a γ-ray sterilization treatment.

Example 15
Immobilization and γ-ray Sterilization Stability of MP47K3 Peptide An adsorbent GCL200mMP47K3 and an adsorbent γGCL200mMP47K3 were obtained in the same way as in Example 13, except that MP47K3 peptide obtained in Example 5 was used. The reaction yield of the peptide with respect to a gel was 42%, and the immobilized amount thereof was 2.6 mg per 1 ml of gel.

The IgG adsorption ratio and the IC adsorption ratio of the GCL2000mMP47K3 or γGCL200mMP47K3 thus obtained are as shown in Table 8. In the GCL2000mMP47K3, using as a ligand recombinant MP47K3 peptide in which Asp at position 47 of the C3 peptide was replaced by Pro, and Lys-Lys-Lys was added to the C-terminus as a functional group for immobilization to a carrier, the γ-ray sterilization stability of an adsorbing capacity with respect to IC and IgG substantially improved, compared with the case where the MK3G56 peptide (comparative example) was used as a carrier.

Example 16
Immobilization and γ-ray Sterilization Stability of MP47 Peptide

Water was added to 90 ml of GC700m (produced by Chisso Corporation, a molecular weight of the exclusion limit of a globular protein: 400,000) which is a cellulose type porous hard gel so that a total volume became 180 ml. Thereafter, 60 ml of 2 M sodium hydroxide was added to the mixture, and the resultant mixture was heated to 40° C. Then, 21 ml of epichlorohydrin was added to the mixture, and the mixture was allowed to react at 40° C. for one hour with stirring. After the completion of the reaction, the reaction product was thoroughly washed with water to obtain an epoxy activated gel.

An adsorbent GC700mMP47 and an adsorbent γGC700mMP47 were obtained in the same way as in Example 13, except that the epoxy activated gel thus obtained and MP47 peptide obtained in Example 6 were used. The reaction yield of the peptide was 42%, and the immobilized amount was 2.6 mg per 1 ml of gel.

The IgG adsorption ratio and the IC adsorption ratio of the GC700mMP47 or γGC700mMP47 thus obtained are as shown in Table 8. In the GC700mMP47, using as a ligand recombinant peptide MP47 in which Asp at position 47 of the C3 peptide was replaced by Pro, γ-ray sterilization stability of the IC and IgG adsorbing capacity substantially improved, compared with the case where recombinant C3 peptide (MG56) described in Example 18 was used as a ligand.

Example 17
Immobilization and γ-ray Sterilization Stability of MP47C Peptide An adsorbent GC700mMP47C and an adsorbent γGC700mMP47C were obtained in the same way as in Example 13, except that the epoxy activated gel obtained in Example 16 and MP47C peptide obtained in Example 7 were used. The reaction yield of the peptide with respect to a gel was 64%, and the immobilized amount was 4.0 mg per 1 ml of gel.

The IgG adsorption ratio and the IC adsorption ratio of the GC700mMP47C or γGC700mMP47C thus obtained are as shown in Table 8. In the GC700mMP47C, using as a ligand recombinant MP47C peptide in which Asp at position 47 of the C3 peptide was replaced by Pro, and -Cys was added to the C-terminus as a functional group for immobilization to a carrier, the adsorption ratio with respect to IC and IgG remarkably improved, compared with the case where the MG56 corresponding to recombinant C3 peptide was used as a ligand in Example 18 and the case where MP47 peptide with no -Cys added to the C-terminus was used as a ligand in Example 16. Furthermore, the adsorbing capacity hardly decreased even after γ-ray sterilization.

Example 18
Immobilization and γ-ray Sterilization Stability of MG56 Peptide An adsorbent GC700mMG56 and an adsorbent γGC700mMG56 were obtained in the same way as in Example 13, except that the epoxy activated gel obtained in Example 16 and MG56 peptide obtained in Example 10 were used. The reaction yield of the peptide with respect to a gel was 64%, and the immobilized amount thereof was 4.0 mg per 1 ml of gel.

The IgG adsorption ratio and the IC adsorption ratio of the GC700mMG56 or γGC700mMG56 thus obtained are as shown in Table 8. The GC700mMG56, using as a ligand MG56 which is a recombinant C3 peptide, exhibited a relatively high adsorption ratio with respect to IC and IgG. However, the GC700mMG56 lost most of its adsorbing capacity after being subjected to a γ-ray sterilization treatment.

Example 19
Immobilization and γ-ray Sterilization Stability of MK3-7M Peptide An adsorbent HW65MK3-7M and an adsorbent γHW65MK3-7M were obtained in the same way as in Example 13, except that 0.3 g of AF-Torecyl Toyopearl 650 was suspended in 3 ml of 0.1 M sodium carbonate buffer containing 0.5 M sodium chloride (pH 9.0) in place of suspending the above-mentioned epoxy activated gel, 10 mg of MK3-7M peptide obtained in Example 9 was added to the suspension, and the resultant suspension was allowed to react at 40° C. for 60 hours with stirring. The reaction yield of the peptide was 57%, and the immobilized amount was 3.6 mg per 1 ml of gel.

The IgG adsorption ratio and the IC adsorption ratio of the HW65MK3-7M or γHW65MK3-7M thus obtained are as shown in Table 8. In the HW65MK3-7M which comprises a recombinant peptide MK3-7M as a ligand, in which 7 mutations were introduced into the C3 peptide, and Lys-Lys-Lys- was added to the N-terminus as a functional group for immobilization to a carrier, γ-ray sterilization stability of the IC and IgG adsorbing capacity substantially improved, compared with the MG56 which is the recombinant C3 peptide described in Example 18.

TABLE 8

| Example | Adsorbent | IgG adsorption ratio (%) | IC adsorption ratio (%) |
|---|---|---|---|
| Example 13 | GCL2000mMK3P47 | 85 | 35 |
|  | γGCL2000mMK3P47 | 75 | 35 |
| Example 14 | GCL2000mMK3G56 | 70 | 30 |
|  | γGCL2000mMK3G56 | 21 | 12 |
| Example 15 | GCL2000mMP47K3 | 70 | 35 |
|  | γGCL2000mMP47K3 | 60 | 30 |
| Example 16 | GC700mMP47 | 60 | 35 |
|  | γGC700mMP47 | 53 | 35 |
| Example 17 | GC700mMP47C | 90 | 65 |
|  | γGC700mMP47C | 82 | 60 |
| Example 18 | GC700mMG56 | 65 | 30 |
|  | γGC700mMG56 | 20 | 10 |
| Example 19 | HW65MK3-7M | 75 | 35 |
|  | γHW65MK3-7M | 65 | 35 |

Example 20
High-pressure Vapor Sterilization Stability of an Adsorbent with a Peptide Derivative Immobilized Thereon A part of the adsorbent GC700mMP47C obtained in Example 17 and a part of the adsorbent GC700mMG56 obtained in Example 18 were each subjected to autoclave sterilization (121° C., 20 minutes) under the condition of being suspended in a saline. Thus, aGC700mMP47C and aGC700mMG56 were obtained, respectively. The IgG adsorption ratio of these adsorbents was calculated by using the method similar to that of Example 13. The results are shown in Table 9.

The GC700mMP47, using as a ligand recombinant peptide MP47C in which Asp at position 47 of the C3 peptide was replaced by Pro, and -Cys was added to a C-terminus as a functional group for immobilization to carriers, exhibited a very high IgG adsorption ratio (50%) after an autoclave treatment, whereas the adsorbent GC700mMG56 obtained in Example 18 using recombinant C3 peptide (MG56) as a ligand completely lost an IgG adsorbing capacity after an autoclave treatment.

TABLE 9

| Adsorbent | IgG adsorption ratio (%) |
|---|---|
| GC700mMG56 | 65 |
| aGC700mMG56 | 0 |
| GC700mMP47C | 90 |
| aGC700MP47C | 50 |

INDUSTRIAL APPLICABILITY

By using an adsorbent with a peptide immobilized thereon of the present invention, immunoglobulins and/or immunoglobulin complexes can be selectively adsorbed and removed, and $IgG_3$ which is not adsorbed by protein A can be adsorbed and removed. Furthermore, the adsorbent of the present invention is inexpensive, and can be subjected to an autoclave sterilization treatment due to its excellent storage stability such as thermal stability. Furthermore, the adsorbent of the present invention can efficiently adsorb and remove immunoglobulins and/or immunoglobulin complexes contained in the body fluid even after the adsorbent is subjected to a drug treatment and a sterilization treatment.

What is claimed is:

1. An adsorbent for adsorbing immunoglobulins and/or immunoglobulin complexes, the adsorbent comprising a peptide comprising the amino acid sequence of a peptide derivative of the amino acid sequence of SEQ ID NO: 1, the peptide being immobilized onto a water-insoluble carrier; and the peptide derivative comprising at least one deletion, substitution, insertion or addition of at least one amino acid as compared to the amino acid sequence of SEQ ID NO: 1, wherein the peptide derivative is improved over a peptide comprising the amino acid sequence of SEQ ID NO: 1 in at least one of the properties of thermal stability, drug stability, γ-ray sterilization stability, and high-pressure vapor sterilization stability.

2. The adsorbent according to claim 1, wherein the peptide derivative comprises an amino acid sequence of SEQ ID NO: 3.

3. The adsorbent according to claim 1 or 2, wherein the peptide further comprises the addition of (Lys)n or (Cys)m to the amino terminus and/or the carboxyl terminus of the peptide derivative, wherein n and m are integers from 1 to 9.

4. The adsorbent according to claim 3, wherein the peptide consists of an amino acid sequence of 70 amino acids or less.

5. The adsorbent according to claim 4, wherein the adsorbent is subjected to high-pressure vapor sterilization or γ-ray sterilization.

6. The adsorbent according to claim 4, wherein the water-insoluble carrier is porous or hydrophilic.

7. The adsorbent according to claim 6, wherein the water-insoluble carrier has a molecular weight exclusion limit in the range of 150,000 to 5,000,000.

8. The adsorbent according to claim 3, wherein the adsorbent is subjected to high-pressure vapor sterilization or γ-ray sterilization.

9. The adsorbent according to claim 3, wherein the water-insoluble carrier is porous or hydrophilic.

10. The adsorbent according to claim 9, wherein the water-insoluble carrier has a molecular weight exclusion limit in the range of 150,000 to 5,000,000.

11. The adsorbent according to claim 1 or 2, wherein the peptide consists of an amino acid sequence of 70 amino acids or less.

12. An adsorbent according to claim 11, wherein the adsorbent is subjected to high-pressure vapor sterilization or γ-ray sterilization.

13. The adsorbent according to claim 11, wherein the water-insoluble carrier is porous or hydrophilic.

14. The adsorbent according to claim 13, wherein the water-insoluble carrier has a molecular weight exclusion limit in the range of 150,000 to 5,000,000.

15. The adsorbent according to claim 1 or 2, wherein the adsorbent is subjected to high-pressure vapor sterilization or γ-ray sterilization.

16. The adsorbent according to claim 1 or 2, wherein the water-insoluble carrier is porous or hydrophilic.

17. The adsorbent according to claim 16, wherein the water-insoluble carrier has a molecular weight exclusion limit in the range of 150,000 to 5,000,000.

18. A method for adsorbing and removing immunoglobulins and/or immunoglobulin complexes from a fluid containing them, comprising the step of bringing the adsorbent of claim 1 or 2 into contact with the fluid containing the immunoglobulins and/or immunoglobulin complexes.

19. The method according to claim 18, wherein the fluid is selected from the group consisting of blood, plasma, and other body fluids obtained from a living organism.

20. A device for adsorbing and removing immunoglobulins and/or immunoglobulin complexes from a fluid containing them, the device comprising a vessel that accommodates the adsorbent of claim 1 or 2, that has an inlet and an outlet for a solution, and that has effluent-preventing means for preventing the adsorbent from flowing out of the vessel.

* * * * *

SEQUENCE LISTING

<160> NUMBER OF SEQ ID NOS: 17

<210> SEQ ID NO 1
<211> LENGTH: 56
<212> TYPE: PRT
<213> ORGANISM: protein G
<220> FEATURE:
<221> NAME/KEY: VARIANT
<222> LOCATION: (6)
<223> OTHER INFORMATION: Val or Ile
<220> FEATURE:
<221> NAME/KEY: VARIANT
<222> LOCATION: (7)
<223> OTHER INFORMATION: Ile or Leu
<220> FEATURE:
<221> NAME/KEY: VARIANT
<222> LOCATION: (19)
<223> OTHER INFORMATION: Lys or Glu
<220> FEATURE:
<221> NAME/KEY: VARIANT
<222> LOCATION: (24)
<223> OTHER INFORMATION: Glu or Ala
<220> FEATURE:
<221> NAME/KEY: VARIANT
<222> LOCATION: (29)
<223> OTHER INFORMATION: Ala or Val
<220> FEATURE:
<221> NAME/KEY: VARIANT
<222> LOCATION: (42)
<223> OTHER INFORMATION: Val or Glu

<400> SEQUENCE: 1

Thr Thr Tyr Lys Leu Xaa Xaa Asn Gly Lys Thr Leu Lys Gly Glu Thr
 1               5                  10                  15

Thr Thr Xaa Ala Val Asp Ala Xaa Thr Ala Glu Lys Xaa Phe Lys Gln
            20                  25                  30

Tyr Ala Asn Asp Asn Gly Val Asp Gly Xaa Trp Thr Tyr Asp Asp Ala
        35                  40                  45

Thr Lys Thr Phe Thr Val Thr Glu
    50                  55

<210> SEQ ID NO 2
<211> LENGTH: 57
<212> TYPE: PRT
<213> ORGANISM: synthetic peptide

<400> SEQUENCE: 2

Cys Thr Thr Tyr Lys Leu Val Ile Asn Gly Lys Thr Leu Lys Gly Glu
 1               5                  10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Asp
        35                  40                  45

Ala Thr Lys Thr Phe Thr Val Thr Glu
    50                  55

<210> SEQ ID NO 3
<211> LENGTH: 56
<212> TYPE: PRT
<213> ORGANISM: synthetic peptide
<220> FEATURE:
<221> NAME/KEY: VARIANT
<222> LOCATION: (6)
<223> OTHER INFORMATION: Val or Ile
<220> FEATURE:
<221> NAME/KEY: VARIANT

```
<222> LOCATION: (7)
<223> OTHER INFORMATION: Ile or Leu
<220> FEATURE:
<221> NAME/KEY: VARIANT
<222> LOCATION: (19)
<223> OTHER INFORMATION: Lys or Glu
<220> FEATURE:
<221> NAME/KEY: VARIANT
<222> LOCATION: (24)
<223> OTHER INFORMATION: Glu or Ala
<220> FEATURE:
<221> NAME/KEY: VARIANT
<222> LOCATION: (29)
<223> OTHER INFORMATION: Ala or Val
<220> FEATURE:
<221> NAME/KEY: VARIANT
<222> LOCATION: (42)
<223> OTHER INFORMATION: Val or Glu
<220> FEATURE:
<221> NAME/KEY: VARIANT
<222> LOCATION: (50)
<223> OTHER INFORMATION: Lys or Gly

<400> SEQUENCE: 3

Thr Thr Tyr Lys Leu Xaa Xaa Asn Gly Lys Thr Leu Lys Gly Glu Thr
 1               5                  10                  15

Thr Thr Xaa Ala Val Asp Ala Xaa Thr Ala Glu Lys Xaa Phe Lys Gln
            20                  25                  30

Tyr Ala Asn Asp Asn Gly Val Asp Gly Xaa Trp Thr Tyr Asp Pro Ala
        35                  40                  45

Thr Xaa Thr Phe Thr Val Thr Glu
    50                  55

<210> SEQ ID NO 4
<211> LENGTH: 60
<212> TYPE: PRT
<213> ORGANISM: synthetic peptide

<400> SEQUENCE: 4

Met Lys Lys Lys Thr Thr Tyr Lys Leu Val Ile Asn Gly Lys Thr Leu
 1               5                  10                  15

Lys Gly Glu Thr Thr Thr Lys Ala Val Asp Ala Glu Thr Ala Glu Lys
            20                  25                  30

Ala Phe Lys Gln Tyr Ala Asn Asp Asn Gly Val Asp Gly Val Trp Thr
        35                  40                  45

Tyr Asp Pro Ala Thr Lys Thr Phe Thr Val Thr Glu
    50                  55                  60

<210> SEQ ID NO 5
<211> LENGTH: 190
<212> TYPE: DNA
<213> ORGANISM: synthetic DNA

<400> SEQUENCE: 5
catatgaaaa agaagaccac ctataaactg gttatcaacg gtaaaaccct gaaaggtgaa      60
accaccacca aggctgttga cgctgaaacc gctgaaaaag catttaaaca gtatgctaac     120
gacaacggtg tcgacggtgt tggacctat gaccccgcta ccaaaaccct taccgttacc     180
gaataagctt                                                           190

<210> SEQ ID NO 6
<211> LENGTH: 60
<212> TYPE: PRT
<213> ORGANISM: synthetic peptide
```

-continued

<400> SEQUENCE: 6

Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Pro
        35                  40                  45

Ala Thr Lys Thr Phe Thr Val Thr Glu Lys Lys Lys
    50                  55                  60

<210> SEQ ID NO 7
<211> LENGTH: 190
<212> TYPE: DNA
<213> ORGANISM: synthetic DNA

<400> SEQUENCE: 7
catatgacca cctataaact gcttatcaac ggtaaaaccc tgaaaggtga aaccaccacc     60
aaggctgttg acgctgaaac cgctgaaaaa gcatttaaac agtatgctaa cgacaacggt    120
gtcgacggtg tttggaccta tgaccccgct accaaaacct ttaccgttac cgaaaaaaag   180
aagtaagctt                                                           190

<210> SEQ ID NO 8
<211> LENGTH: 57
<212> TYPE: PRT
<213> ORGANISM: synthetic peptide

<400> SEQUENCE: 8

Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Pro
        35                  40                  45

Ala Thr Lys Thr Phe Thr Val Thr Glu
    50                  55

<210> SEQ ID NO 9
<211> LENGTH: 181
<212> TYPE: DNA
<213> ORGANISM: synthetic DNA

<400> SEQUENCE: 9
catatgacca cctataaact ggttatcaac ggtaaaaccc tgaaaggtga aaccaccacc     60
aaggctgttg acgctgaaac cgctgaaaaa gcatttaaac agtatgctaa cgacaacggt    120
gtcgacggtg tttggaccta tgaccccgct accaaaacct ttaccgttac cgaataagct   180
t                                                                    181

<210> SEQ ID NO 10
<211> LENGTH: 58
<212> TYPE: PRT
<213> ORGANISM: synthetic peptide

<400> SEQUENCE: 10

Met Thr Thr Tyr Lys Leu Val Ile Asn Gly Lys Thr Leu Lys Gly Glu
1               5                   10                  15

Thr Thr Thr Lys Ala Val Asp Ala Glu Thr Ala Glu Lys Ala Phe Lys
            20                  25                  30

Gln Tyr Ala Asn Asp Asn Gly Val Asp Gly Val Trp Thr Tyr Asp Pro
          35                  40                  45

Ala Thr Lys Thr Phe Thr Val Thr Glu Cys
        50                  55

<210> SEQ ID NO 11
<211> LENGTH: 184
<212> TYPE: DNA
<213> ORGANISM: synthetic DNA

<400> SEQUENCE: 11
catatgacca cctataaact ggttatcaac ggtaaaaccc tgaaaggtga aaccaccacc      60
aaggctgttg acgctgaaac cgctgaaaaa gcatttaaac agtatgctaa cgacaacggt     120
gtcgacggtg tttggaccta tgaccccgct accaaaacct ttaccgttac cgaatgctaa    180
gctt                                                                   184

<210> SEQ ID NO 12
<211> LENGTH: 60
<212> TYPE: PRT
<213> ORGANISM: synthetic peptide

<400> SEQUENCE: 12

Met Lys Lys Lys Thr Thr Tyr Lys Leu Val Ile Asn Gly Lys Thr Leu
 1               5                  10                  15

Lys Gly Glu Thr Thr Thr Lys Ala Val Asp Ala Glu Thr Ala Glu Lys
            20                  25                  30

Ala Phe Lys Gln Tyr Ala Asn Asp Asn Gly Val Asp Gly Val Trp Thr
        35                  40                  45

Tyr Asp Asp Ala Thr Lys Thr Phe Thr Val Thr Glu
    50                  55                  60

<210> SEQ ID NO 13
<211> LENGTH: 190
<212> TYPE: DNA
<213> ORGANISM: synthetic DNA

<400> SEQUENCE: 13
catatgaaaa agaagaccac ctataaactg gttatcaacg gtaaaaccct gaaaggtgaa      60
accaccacca aggctgttga cgctgaaacc gctgaaaaag catttaaaca gtatgctaac     120
gacaacggtg tcgacggtgt ttggacctat gacgacgcta ccaaaacctt taccgttacc    180
gaataagctt                                                             190

<210> SEQ ID NO 14
<211> LENGTH: 60
<212> TYPE: PRT
<213> ORGANISM: synthetic peptide

<400> SEQUENCE: 14

Met Lys Lys Lys Thr Thr Tyr Lys Leu Ile Leu Asn Gly Lys Thr Leu
 1               5                  10                  15

Lys Gly Glu Thr Thr Thr Lys Ala Val Asp Ala Ala Thr Ala Glu Lys
            20                  25                  30

Val Phe Lys Gln Tyr Ala Asn Asp Asn Gly Val Asp Gly Glu Trp Thr
        35                  40                  45

Tyr Asp Pro Ala Thr Lys Thr Phe Thr Val Thr Glu
    50                  55                  60

<210> SEQ ID NO 15
<211> LENGTH: 190
<212> TYPE: DNA
<213> ORGANISM: synthetic DNA

<400> SEQUENCE: 15

```
catatgaaaa agaagaccac ctataaactg atcctgaacg gtaaaaccat aaaaggtgaa      60
accaccaccg gagctgttga cgctgctacc gctgaaaaag tttttaaaca gtatgctaac     120
gacaacggtg tcgacggtga atggacctat gacgacgcta ccaaaacctt taccgttacc    180
gaataagctt                                                            190
```

<210> SEQ ID NO 16
<211> LENGTH: 57
<212> TYPE: PRT
<213> ORGANISM: synthetic peptide

<400> SEQUENCE: 16

```
Met Thr Thr Tyr Lys Leu Val Ile Asn Gly Lys Thr Leu Lys Gly Glu
  1               5                  10                  15

Thr Thr Thr Lys Ala Val Asp Ala Glu Thr Ala Glu Lys Ala Phe Lys
                 20                  25                  30

Gln Tyr Ala Asn Asp Asn Gly Val Asp Gly Val Trp Thr Tyr Asp Asp
             35                  40                  45

Ala Thr Lys Thr Phe Thr Val Thr Glu
         50                  55
```

<210> SEQ ID NO 17
<211> LENGTH: 181
<212> TYPE: DNA
<213> ORGANISM: synthetic DNA

<400> SEQUENCE: 17

```
catatgacca cctataaact ggttatcaac ggtaaaaccc tgaaaggtga aaccaccacc      60
aaggctgttg acgctgaaac cgctgaaaaa gcatttaaac agtatgctaa cgacaacggt    120
gtcgacggtg tttggaccta tgacgacgct accaaaacct ttaccgttac cgaataagct    180
t                                                                     181
```